US011614448B2

(12) United States Patent
Prieur

(10) Patent No.: US 11,614,448 B2
(45) Date of Patent: Mar. 28, 2023

(54) COMPOSITIONS AND METHODS FOR DETECTING PROSTATE CANCER

(71) Applicant: ECS-Progastrin SA, Prilly (CH)

(72) Inventor: Alexandre Prieur, Montpellier (FR)

(73) Assignee: ECS-Progastrin SA, Montpellier (FR)

( * ) Notice: Subject to any disclaimer, the term of this patent is extended or adjusted under 35 U.S.C. 154(b) by 313 days.

(21) Appl. No.: 16/498,543

(22) PCT Filed: Mar. 30, 2018

(86) PCT No.: PCT/EP2018/058330
§ 371 (c)(1),
(2) Date: Sep. 27, 2019

(87) PCT Pub. No.: WO2018/178352
PCT Pub. Date: Oct. 4, 2018

(65) Prior Publication Data
US 2020/0200751 A1 Jun. 25, 2020

(30) Foreign Application Priority Data

Mar. 30, 2017 (EP) .................................... 17305381

(51) Int. Cl.
| G01N 33/574 | (2006.01) |
| C07K 16/26 | (2006.01) |
| C07K 16/30 | (2006.01) |
| A61P 35/00 | (2006.01) |
| A61K 39/395 | (2006.01) |
| A61K 45/06 | (2006.01) |
| C07K 16/22 | (2006.01) |
| C07K 16/28 | (2006.01) |
| A61K 39/00 | (2006.01) |

(52) U.S. Cl.
CPC ... *G01N 33/57434* (2013.01); *A61K 39/3955* (2013.01); *A61K 39/39541* (2013.01); *A61K 45/06* (2013.01); *A61P 35/00* (2018.01); *C07K 16/22* (2013.01); *C07K 16/26* (2013.01); *C07K 16/2863* (2013.01); *C07K 16/3069* (2013.01); *G01N 33/5748* (2013.01); *A61K 2039/507* (2013.01); *C07K 2317/22* (2013.01); *C07K 2317/24* (2013.01); *C07K 2317/51* (2013.01); *C07K 2317/515* (2013.01); *C07K 2317/56* (2013.01); *C07K 2317/565* (2013.01); *C07K 2317/622* (2013.01); *C07K 2317/76* (2013.01); *G01N 2333/96411* (2013.01)

(58) Field of Classification Search
CPC ........ G01N 33/57434; G01N 33/5748; G01N 2333/96411; C07K 16/26; C07K 16/3069; C07K 2317/22; C07K 2317/565
See application file for complete search history.

(56) References Cited

U.S. PATENT DOCUMENTS

| 4,444,887 A | 4/1984 | Hoffmann |
| 4,716,111 A | 12/1987 | Osband et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,585,089 A | 12/1996 | Queen et al. |
| 5,639,641 A | 6/1997 | Pedersen et al. |
| 5,693,761 A | 12/1997 | Queen et al. |
| 5,814,318 A | 9/1998 | Lonberg et al. |
| 5,877,293 A | 3/1999 | Adair et al. |
| 5,886,152 A | 3/1999 | Nakatani et al. |
| 6,054,297 A | 4/2000 | Carter et al. |
| 6,180,370 B1 | 1/2001 | Queen et al. |
| 2013/0095503 A1* | 4/2013 | Lu .................... G01N 33/57488 435/7.4 |

FOREIGN PATENT DOCUMENTS

| EP | 0 451 261 B1 | 9/1993 |
| EP | 0 682 040 B1 | 8/1999 |
| EP | 0 566 647 B1 | 10/2003 |
| EP | 0 592 106 B1 | 11/2004 |
| EP | 0 519 596 B1 | 2/2005 |
| EP | 0 939 127 B1 | 9/2014 |
| WO | WO 91/10741 A1 | 7/1991 |
| WO | WO 96/33735 A1 | 10/1996 |
| WO | WO 96/34096 A1 | 10/1996 |
| WO | WO 98/16654 A1 | 4/1998 |
| WO | WO 98/24893 A2 | 6/1998 |
| WO | WO 98/46645 A2 | 10/1998 |
| WO | WO 98/50433 A2 | 11/1998 |
| WO | WO 2006/032980 A1 | 3/2006 |
| WO | WO 2011/083088 A2 | 7/2011 |
| WO | WO 2011/083089 A1 | 7/2011 |
| WO | WO 2011/083090 A2 | 7/2011 |
| WO | WO 2011/083091 A2 | 7/2011 |
| WO | WO 2011/116954 A2 | 9/2011 |
| WO | WO 2012/013609 A1 | 2/2012 |
| WO | WO 2015/075445 A1 | 5/2015 |
| WO | WO 2016/145139 A1 | 9/2016 |
| WO | WO 2017/114973 | 7/2017 |

OTHER PUBLICATIONS

Ferrand et al, Biochimica et Biophysica Acta 1793 (2009) 477-488. (Year: 2009).*
Malia et al., Proteins, 2016; 84:427-434. (Year: 2016).*
Barthelemy et al., Journal of Biological Chemistry, 2008, 283:3639-3654. (Year: 2008).*
Beiboer et al., Journal of Molecular Biology, 2000, 296:833-849. (Year: 2000).*

(Continued)

Primary Examiner — Julie Wu
Assistant Examiner — Cheom-Gil Cheong
(74) Attorney, Agent, or Firm — Panitch Schwarze Belisario & Nadel LLP; Erin M. Dunston

(57) ABSTRACT

The present invention relates to compositions and methods for the in vitro diagnosis of prostate cancer, wherein said compositions comprise an antibody binding to progastrin and said methods comprise the use of an antibody binding to progastrin.

15 Claims, 1 Drawing Sheet
Specification includes a Sequence Listing.

(56) References Cited

OTHER PUBLICATIONS

Choi et al., 2011, Molecular BioSystems, 2011, 7:3327-334. (Year: 2011).*
De Genst et al., Developmental and Comparative Immunology, 2006, 30:187-98. (Year: 2006).*
Griffiths et al., The EMBO Journal, 1993, 12:725-734. (Year: 1993).*
Klimka et al., British Journal of Cancer, 2000, 83:252-260. (Year: 2000).*
Ward et al., Nature, 1989, 341:544-546. (Year: 1989).*
Lloyd et al, Protein Engineering Design & Selection (2009) 22:159-168. (Year: 2009).*
Edwards et al, J Mol Biol (2003) 14;334(1):103-118. (Year: 2003).*
Goel et al., The Journal of Immunology (2004) 173(12):7358-7367. (Year: 2004).*
Cornelio ef al., *Gastrin-releasing peptide receptor as a molecular target in experimental anticancer therapy*, 18(9) Annals of Oncology 1457-1466 (Aug. 2007).
Gaudreau et al., *The Present and Future of Biomarkers in Prostate Cancer: Proteomics, Genomics, and Immunology Advancements*, 8(S2) Biomarkers in Cancer 15-33 (2016).
Ischia et al., *Gastrin-releasing peptide: Different forms, different functions*, 35(1) BioFactors 69-75 (Jan./Feb. 2009).
Jones et al., *Replacing the complementarity-determining regions in a human antibody with those from a mouse*, 321 Nature 522-525 (May 29, 1986).
Kaas ef al., *IMGT/3Dstructure-DB and IMGT/StructuralQuery, a database and a tool for immunoglobulin, T cell receptor and MHC structural data*, 32 Nucleic Acids Research D208-D210 (Jan. 2004).
Kaas et al., *IMGT Colliers de Perles: Standardized Sequence-Structure Representations of the IgSF and MhcSF Superfamily Domains*, 2(1) Current Bioinformatics 21-30 (Jan. 2007).
LeFranc, *Unique database numbering system for immunogenetic analysis*, 18(11) Immunology Today 509 (Nov. 1997).
LeFranc, *The IMGT Unique Numbering for Immunoglobulins, T-Cell Receptors, and Ig-Like Domains*, 7(4) The Immunologist 132-136 (1999).
LeFranc et al., *IMGT unique numbering for immunoglobulin and T cell receptor variable domains and Ig superfamily V-like domains*, 27(1) Developmental and Comparative Immunology 55-77 (Jan. 2003).
McGrath et al., *Prostate cancer biomarkers: Are we hitting the mark?*, 4(4) Prostate International 130-135 (Dec. 2016).
Nagakawa et al., *Serum Pro-Gastrin-Releasing Peptide (31-98) in Benign Prostatic Hyperplasia and Prostatic Carcinoma*, 60(3) Urology 527-530 (Sep. 2002).
Padlan, *A Possible Procedure for Reducing the Immunogenicity of Antibody Variable Domains While Preserving Their Ligand-Binding Properties*, 28(4/5) Molecular Immunology 489-498 (1991).
Roguska et al., *Humanization of murine monoclonal antibodies through variable domain resurfacing*, 91(3) Proc. Natl. Acad. Sci. USA 969-973 (Feb. 1994).
Ruiz et al., *IMGT Gene Identification and Colliers de Perles of Human Immunoglobulins with known 3D Structures*, 53 (10/11) Immunogenetics 857-883 (Feb. 2002).
Saini, *PSA and beyond: alternative prostate cancer biomarkers*, 39(2) Cell Oncol (DORDR) 97-106 (Apr. 2016).
Singer et al., *Optimal Humanization of 1B4, an Anti-CD18 Murine Monoclonal Antibody, Is Achieved by Correct Choice of Human V-Region Framework Sequences*, 150(7) The Journal of Immunology 2844-2857 (Apr. 1, 1993).
Studnicka et al., *Human-engineered monoclonal antibodies retain full specific binding activity by preserving non-CDR complementarity-modulating residues*, 7(6) Protein Engineering 805-814 (1994).
Yashi et al., *Bioactive Neuropeptide Precursor, Progastrin-Releasing Peptide (Progrp) is a Distinct Prognostic Marker in Metastatic and Hormone-Refractory Prostate Cancer*, 7(3) European Urology Supplements 207 (Mar. 2008).
Yashi et al., *Elevated Serum Progastrin-Releasing Peptide (31-98) in Metastatic and Androgen-Independent Prostate Cancer Patients*, 51 (2) The Prostate 84-97 (May 2002).
Yashi et al., *Elevated Serum Progastrin-Releasing Peptide (31-98) Level is a Predictor of Short Response Duration After Hormonal Therapy in Metastatic Prostate Cancer*, 56(4) The Prostate 305-312 (Sep. 2003).
International Search Report (Form PCT/ISA/210) dated May 22, 2018, by the European Patent Office in corresponding International Application No. PCT/EP2018/058330. (4 pages).

* cited by examiner

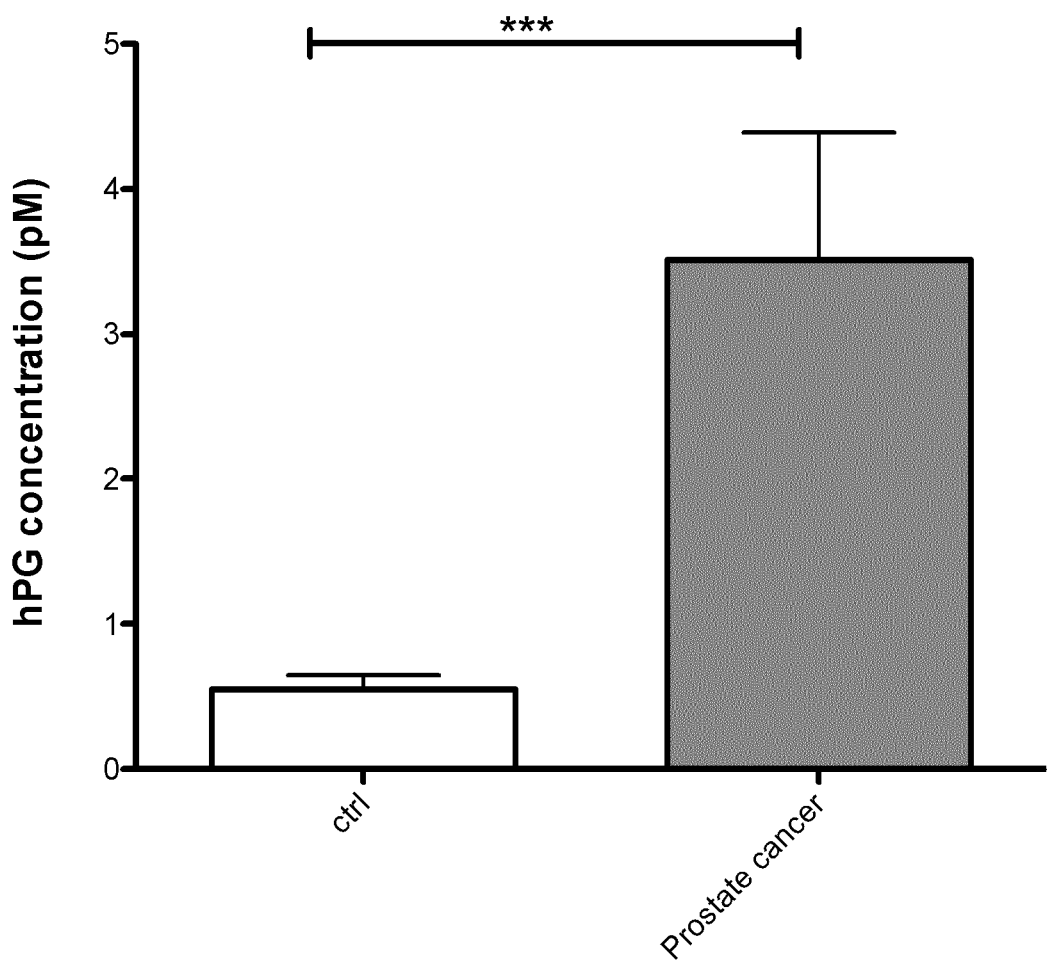

COMPOSITIONS AND METHODS FOR DETECTING PROSTATE CANCER

INTRODUCTION

The present invention relates to the in vitro diagnosis of cancer, more particularly it relates to methods for the in vitro diagnosis of prostate cancer. Compositions according to the invention comprise a progastrin-binding molecule, in particularly an anti-hPG antibody, whereas methods according to the invention comprise the use of a progastrin-binding molecule, and particularly to an anti-hPG antibody.

According to the International Agency for Cancer Research, prostate cancer (PC) is the second most common cancer in men and the fifth leading cause of cancer-related death in men. In 2012 it occurred in 1.1 million men and caused 307,000 deaths. In the United States, it is the most common non-cutaneous cancer in men in the United States. An estimated one in six white men and one in five African-American men will be diagnosed with prostate cancer in their lifetime, with the likelihood increasing with age.

Most prostate cancers (95%) are adenocarcinoma, or glandular cancers, that begin when normal semen-secreting prostate gland cells mutate into cancer cells. Approximately 4% of cases of prostate cancer have transitional cell morphology and are thought to arise from the urothelial lining of the prostatic urethra. The few cases that have neuroendocrine morphology are believed to arise from the neuroendocrine stem cells normally present in the prostate or from aberrant differentiation programs during cell transformation. Squamous cell carcinomas constitute less than 1% of all prostate carcinomas. Prostate cancer most commonly metastasizes to the bones, lymph nodes, and may invade rectum, bladder and lower ureters after local progression.

Treatments usually include surgery, chemotherapy, radiation therapy, and targeted therapy, alone or in combination. However, outcomes are often poor with a less than 10% 5-year survival rate globally. This is largely because most people are detected only with advanced disease, which has a direct consequence on the survival rate. In some Asian countries, screening efforts have shown to be associated with a higher survival rates.

The five-year survival rate of the overall population of prostate cancer is very high (ca. 99%). However, this rate drops considerably when the cancer is metastasized (ca. 28.5%). Fortunately, ca. 80% of the patients are diagnosed with localized disease (Surveillance E; End Results Program (SEER). Surveillance, Epidemiology, and Ends Results Program. Fast Stats; 2016 [cited 12 Sep. 2016]. Available at: seer.cancer.gov). This is due in large part to improvements in screening methods. However, the most commonly-used biomarker prostate-specific antigen (PSA) has proven controversial as a diagnostic assay due to its limitations.

Therefore, there is still a need for methods allowing a quick, reliable and cost-effective diagnosis of prostate cancer.

This is the object of the present invention.

BRIEF DESCRIPTION OF THE DRAWINGS

FIG. 1

Progastrin concentration was measured in 40 plasma samples from prostate cancer patients and 119 plasma samples from healthy donors using the ELISA Kit DECODE Lab (capture antibody: Mab14, detection antibody: anti-hPG polyclonal).

DESCRIPTION

The present invention now provides methods for the in vitro diagnosis of prostate cancer, wherein said method comprises the detection progastrin in a biological sample from a subject. Preferably, the amount of progastrin in said sample is determined, thus allowing quantification of progastrin.

Human pre-progastrin, a 101 amino acids peptide (Amino acid sequence reference: AAB19304.1), is the primary translation product of the gastrin gene. Progastrin is formed by cleavage of the first 21 amino acids (the signal peptide) from preprogastrin. The 80 amino-acid chain of progastrin is further processed by cleavage and modifying enzymes to several biologically active gastrin hormone forms: gastrin 34 (G34) and glycine-extended gastrin 34 (G34-Gly), comprising amino acids 38-71 of progastrin, gastrin 17 (G17) and glycine-extended gastrin 17 (G17-Gly), comprising amino acids 55 to 71 of progastrin.

Anti-human progastrin (anti-hPG) monoclonal antibodies and their use for therapy have been described in the following documents: WO 2011/083 088 for colorectal cancer, WO 2011/083 090 for breast cancer, WO 2011/083 091 for pancreatic cancer, WO 2011/116 954 for colorectal and gastrointestinal cancer, and WO 2012/013 609 and WO 2011/083089 for liver pathologies.

The present invention will become more fully understood from the detailed description given herein and from the accompanying drawings, which are given by way of illustration only and do not limit the intended scope of the invention.

In a first aspect, the present invention relates to a method for the in vitro evaluation of a risk of the presence of prostate cancer, wherein said method comprises a step of detecting progastrin in a biological sample from a subject. The presence of progastrin in the sample indicates that there is a risk of the presence of prostate cancer.

Thus, in a first embodiment, the invention relates to an in vitro method for evaluating the risk of the presence of prostate cancer in a subject, said method comprising the steps of:
  a) contacting a biological sample from said subject with at least one progastrin-binding molecule, and
  b) detecting the binding of said progastrin-binding molecule to progastrin in said sample, wherein said binding indicates a risk of the presence of prostate cancer.

The binding of progastrin-binding molecule may be detected by various assays available to the skilled artisan. Although any suitable means for carrying out the assays are included within the invention, it can be mentioned in particular FACS, ELISA, RIA, western-blot and IHC.

In a preferred embodiment, the method according to the invention for the in vitro evaluation of a risk of the presence of prostate cancer in a subject, comprises the steps of:
  a) contacting said biological sample from said subject with at least one progastrin-binding molecule,
  b) determining the concentration of progastrin in said biological sample, wherein a concentration of progastrin of at least 10 pM in said biological sample is indicative of a risk of the presence of prostate cancer.

Once the concentration of progastrin present in the sample is determined, the result can be compared with those of control sample(s), which is (are) obtained in a manner similar to the test samples but from individual(s)s known not to suffer from a prostate cancer. If the concentration of progastrin is significantly more elevated in the test sample, it may be concluded that there is an increased likelihood that the subject from whom it was derived has a prostate cancer.

Thus, in a more preferred embodiment, the method of the invention comprises the further steps of:
- c) determining a reference concentration of progastrin in a reference sample,
- d) comparing the concentration of progastrin in said biological sample with said reference concentration of progastrin,
- e) evaluating, from the comparison of step d), the risk of the presence of prostate cancer.

According to another aspect, the invention relates to an in vitro method for diagnosing prostate cancer in a subject, said method comprising the steps of:
- a) contacting a biological sample from said subject with at least one progastrin-binding molecule, and
- b) detecting the binding of said progastrin-binding molecule to progastrin in said sample, wherein said binding indicated the presence of prostate cancer in said subject.

In a preferred embodiment, the present invention relates to a method for the in vitro diagnosis of prostate cancer in a subject, comprising the steps of:
- a) contacting said biological sample from said subject with at least one progastrin-binding molecule,
- b) determining concentration of progastrin in said biological sample, wherein a concentration of progastrin of at least 10 pM in said biological sample is indicative of the presence of prostate cancer in said subject.

In a more particular embodiment of a method according to the invention, a concentration of progastrin of at least 10 pM, at least 20 pM, at least 30 pM, in said biological sample is indicative of the presence of prostate cancer in said subject.

In a more preferred embodiment, the method of the invention comprises the further steps of:
- a) determining a reference concentration of progastrin in a reference sample,
- b) comparing the concentration of progastrin in said biological sample with said reference level or concentration of progastrin,
- c) diagnosing, from the comparison of step d), the presence of prostate cancer.

According to another aspect, the invention relates to an in vitro method for diagnosing metastasized prostate cancer in a subject, said method comprising the steps of:
- a) contacting biological sample from said subject with at least one progastrin-binding molecule, and
- b) detecting the binding of said progastrin-binding molecule to progastrin in said sample, wherein said binding indicates the presence of metastasized prostate cancer in said subject.

In a preferred embodiment, the present invention relates to a method for the in vitro diagnosis of metastasized prostate cancer in a subject, from a biological sample of said subject, comprising the steps of:
- a) contacting said biological sample with at least one progastrin-binding molecule,
- b) determining by a biochemical assay the level or concentration of progastrin in said biological sample, wherein a concentration of progastrin of at least 10 pM higher in said biological sample is indicative of the presence of metastasized prostate cancer in said subject.

In a more particular embodiment of a method according to the invention, a concentration of progastrin of at least 10 pM, at least 20 pM, at least 30 pM, at least 40 pM or at least 50 pM in said biological sample is indicative of the presence of metastasized prostate cancer in said subject.

In a more preferred embodiment, the method of the invention comprises the further steps of:
- a) determining a reference concentration of progastrin in a reference sample,
- b) comparing the concentration of progastrin in said biological sample with said reference concentration of progastrin,
- c) diagnosing, from the comparison of step d), the presence of metastasized prostate cancer.

In a particular embodiment, the present invention relates to a method for the in vitro diagnosis of prostate cancer in a subject, comprising the determination of the concentration of progastrin in a biological sample and comparing said value obtained to the concentration of progastrin in a reference sample.

In a more particular embodiment, in a method for the diagnosis of prostate cancer according to the present invention, the biological sample of said subject is contacted with at least one progastrin-binding molecule, wherein said progastrin-binding molecule is an antibody, or an antigen-binding fragment thereof.

The expression "evaluation of a risk of the presence of prostate cancer in a subject" designates the determination of a relative probability for a given subject to suffer from prostate cancer, when compared to a reference subject or value. A method according to the invention represents a tool in the evaluation of said risk, in combination with other methods or indicators such as clinical examination, biopsy and determination of the level of a known biomarker of prostate cancer, such as, for example, prostate-specific antigen (PSA).

The expression "in vitro diagnosis" means to determine if a subject is suffering from a particular affection. It is known that the diagnosis of prostate cancer involves at least a clinical observation of the symptoms of said subject and of the detection of PSA. PSA testing is currently used as a biomarker. However, PSA does not represent an ideal biomarker, notably because of the general uncertainty regarding its significance, which led the US Preventive Services Task Force to recommend against the use of PDA levels for screening in 2012 (Gaudreau et al, Biomark Cancer. 2016, 8(Suppl 2): 15-33). Although some biomarkers were identified in the discovery phase, it is still a major challenge to transfer them into the clinic, mostly because of the lack of a systematic evaluation process (McGrath et al., Prostate Int. 2016, 4(4): 130-135; Gaudreau et al, Biomark Cancer. 2016, 8(Suppl 2): 15-33; Saini, Cell Oncol (Dordr). 2016, 39(2): 97-106).

Therefore, a method for the in vitro diagnosis of prostate cancer, according to the present invention can be considered as a tool within a diagnosis process.

In a more particular embodiment, the present invention relates to a method for the in vitro diagnosis of prostate cancer in a subject, comprises the determination of the concentration of progastrin in said biological sample and the determination of a known biomarker of prostate cancer, preferably PSA.

The expression "prostate cancer" refers to any type of cancer originating in the prostate. Prostate cancer includes in particular "prostate adenocarcinoma", but also sarcomas, small cell carcinomas, neuroendocrine tumors, transitional cell carcinomas which may also develop within the prostate. The expression "prostate cancer" also involves prostate cancer associated with metastasis, in particular metastasis to the bones, lymph nodes, but also to the rectum, bladder and lower ureters.

The term "progastrin" designates the mammalian progastrin peptide, and particularly human progastrin. For the avoidance of doubt, without any specification, the expression "human progastrin" refers to the human PG of sequence SEQ ID NO:1. Human progastrin comprises notably a N-terminus and a C-terminus domains which are not present in the biologically active gastrin hormone forms mentioned above. Preferably, the sequence of said N-terminus domain is represented by SEQ ID NO:2. In another preferred embodiment, the sequence of said C-terminus domain is represented by SEQ ID NO:3.

The determination of the concentration of progastrin, in a method according to the invention, is performed by any method known by one skilled in the art of biochemistry.

Preferably, determining the levels of progastrin in a sample includes contacting said sample with a progastrin-binding molecule and measuring the binding of said progastrin-binding molecule to progastrin.

When expression levels are measured at the protein level, it may be notably performed using specific progastrin-binding molecules, such as e.g., antibodies, in particular using well known technologies such as cell membrane staining using biotinylation or other equivalent techniques followed by immunoprecipitation with specific antibodies, western blot, ELISA or ELISPOT, enzyme-linked immunosorbant assays (ELISA), radioimmunoassays (RIA), immunohistochemistry (IHC), immunofluorescence (IF), antibodies microarrays, or tissue microarrays coupled to immunohistochemistry. Other suitable techniques include FRET or BRET, single cell microscopic or histochemistry methods using single or multiple excitation wavelength and applying any of the adapted optical methods, such as electrochemical methods (voltametry and amperometry techniques), atomic force microscopy, and radio frequency methods, e.g. multipolar resonance spectroscopy, confocal and non-confocal, detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry), cell ELISA, flow cytometry, radioisotopic, magnetic resonance imaging, analysis by polyacrylamide gel electrophoresis (SDS-PAGE); HPLC-Mass Spectroscopy; Liquid Chromatography/Mass Spectrometry/Mass Spectrometry (LC-MS/MS)). All these techniques are well known in the art and need not be further detailed here. These different techniques can be used to measure the progastrin levels.

Said method may in particular be chosen among: a method based on immuno-detection, a method based on western blot, a method based on mass spectrometry, a method based on chromatography, and a method based on flow cytometry. Although any suitable means for carrying out the assays are included within the invention, methods such as FACS, ELISA, RIA, western-blot and IHC are particularly useful for carrying out the method of the invention.

In a more particular embodiment, a method for the in vitro diagnosis of prostate cancer according to the invention comprises contacting a biological sample from a subject with a progastrin binding molecule using an immunoenzymatic assay, preferably based on techniques chosen among RIA and ELISA.

A "biological sample" as used herein is a sample of biological tissue or fluid that contains nucleic acids or polypeptides, e.g., of a prostate cancer protein, polynucleotide or transcript. Such a sample must allow for the determination of the expression levels of progastrin. Progastrin is known to be a secreted protein. Preferred biological samples for the determination of the level of the progastrin protein thus include biological fluids. A "biological fluid" as used herein means any fluid that includes material of biological origin. Preferred biological fluids for use in the present invention include bodily fluids of an animal, e.g. a mammal, preferably a human subject. The bodily fluid may be any bodily fluid, including but not limited to blood, plasma, serum, lymph, cerebrospinal fluid (CSF), saliva, sweat and urine. Preferably, said preferred liquid biological samples include samples such as a blood sample, a plasma sample, or a serum sample. More preferably, the biological sample is a blood sample. Indeed, such a blood sample may be obtained by a completely harmless blood collection from the patient and thus allows for a non-invasive assessment of the risks that the subject will develop a tumor.

A "biological sample" as used herein also includes a solid cancer sample of the patient to be tested, when the cancer is a solid cancer. Such solid cancer sample allows the skilled person to perform any type of measurement of the level of the biomarker of the invention. In some cases, the methods according to the invention may further comprise a preliminary step of taking a solid cancer sample from the patient. By a "solid cancer sample", it is referred to a tumor tissue sample. Even in a cancerous patient, the tissue which is the site of the tumor still comprises non-tumor healthy tissue. The "cancer sample" should thus be limited to tumor tissue taken from the patient. Said "cancer sample" may be a biopsy sample or a sample taken from a surgical resection therapy.

A biological sample is typically obtained from a eukaryotic organism, most preferably a mammal, or a bird, reptile, or fish. Indeed, a "subject" which may be subjected to the method described herein may be any of mammalian animals including human, dog, cat, cattle, goat, pig, swine, sheep and monkey; or a bird; reptile; or fish. Preferably, a subject is a human being; a human subject may be known as a "patient".

By "obtaining a biological sample," it is herein meant to obtain a biological sample for use in methods described in this invention. Most often, this will be done by removing a sample of cells from an animal, but can also be accomplished by using previously isolated cells (e.g., isolated by another person, at another time, and/or for another purpose), or by performing the methods of the invention in vivo. Archival tissues, having treatment or outcome history, will be particularly useful.

This sample may be obtained and if necessary prepared according to methods known to a person skilled in the art. In particular, it is well known in the art that the sample should be taken from a fasting subject.

The determination of the concentration of progastrin relates to the determination of the quantity of progastrin in known volume of a sample. The concentration of progastrin may be expressed relatively to a reference sample, for example as a ratio or a percentage. The concentration may also be expressed as the intensity or localization of a signal, depending on the method used for the determination of said concentration. Preferably, the concentration of a compound in a sample is expressed after normalization of the total concentration of related compounds in said sample, for example the level or concentration of a protein is expressed after normalization of the total concentration of proteins in the sample.

Preferably, the risk that said subject suffers from prostate cancer is determined by comparing the level of progastrin measured in said biological sample with a reference level.

The term "reference level", as used herein, refers to the expression level of the prostate cancer marker under consideration, i.e. progastrin, in a reference sample. A "reference sample", as used herein, means a sample obtained from subjects, preferably two or more subjects, known to be free of the disease or, alternatively, from the general population. The suitable reference expression levels of progastrin can be determined by measuring the expression levels of said marker in several suitable subjects, and such reference levels can be adjusted to specific subject populations. The reference value or reference level can be an absolute value; a relative value; a value that has an upper or a lower limit; a range of values; an average value; a median value, a mean value, or a value as compared to a particular control or baseline value. A reference value can be based on an individual sample value such as, for example, a value obtained from a sample from the subject being tested, but at an earlier point in time. The reference value can be based on a large number of samples, such as from population of subjects of the chronological age matched group, or based on a pool of samples including or excluding the sample to be tested.

Advantageously, a "reference level" is a predetermined progastrin level, obtained from a biological sample from a subject with a known particular status as regards cancer. In particular embodiments, the reference level used for comparison with the test sample in step (b) may have been obtained from a biological sample from a healthy subject, or from a biological sample from a subject suffering from cancer; it is understood that the reference expression profile can also be obtained from a pool of biological samples of healthy subjects or from a pool of samples from subjects having cancer.

In a particular embodiment of the method of the invention, the reference sample is collected from subjects exempt from any cancer, and preferably from any pathology. It is to be understood that, according to the nature of the biological sample collected from a patient, the reference sample will be a biological sample of the same nature of said biological sample.

The level of progastrin is determined in the present method by determining the amount of progastrin which is bound by a progastrin-binding molecule, preferably by an antibody recognising progastrin.

By "progastrin-binding molecule", it is herein referred to any molecule that binds progastrin, but does not bind gastrin-17 (G17), gastrin-34 (G34), glycine-extended gastrin-17 (G17-Gly), or glycine-extended gastrin-34 (G34-Gly). The progastrin-binding molecule of the present invention may be any progastrin-binding molecule, such as, for instance, an antibody molecule or a receptor molecule. Preferably, the progastrin-binding molecule is an anti-progastrin antibody or an antigen-binding fragment thereof.

According to a particular embodiment, the present invention relates to an in vitro diagnosis method of a prostate cancer comprising the determination of the concentration of progastrin in a biological sample from a subject, wherein said subject exhibits at least one clinical symptom of prostate cancer.

According to another particular embodiment, the present invention relates to an in vitro diagnosis method of a prostate cancer comprising the determination of the concentration of progastrin in a biological sample from a subject, wherein said subject exhibits at least one clinical symptom of cancer and/or of metastasis.

By "binding", "binds", or the like, it is intended that the antibody, or antigen binding fragment thereof, forms a complex with an antigen which, under physiologic conditions, is relatively stable. Methods for determining whether two molecules bind are well known in the art and include, for example, equilibrium dialysis, surface plasmon resonance, and the like. In a particular embodiment, said antibody, or antigen-binding fragment thereof, binds to progastrin with an affinity that is at least two-fold greater than its affinity for binding to a non-specific molecule such as BSA or casein. In a more particular embodiment, said antibody, or antigen-binding fragment thereof, binds only to progastrin.

In a particular embodiment, in a method for the diagnosis of prostate cancer according to the invention, a biological sample from the subject is contacted with at least one progastrin-binding molecule, wherein the affinity of said molecule for progastrin is of at least 100 nM, at least 90 nM, at least 80 nM, at least 70 nM, at least 60 nM, at least 50 nM, at least 40 nM, at least 30 nM, at least 20 nM, at least 10 nM, at least 5 nM, at least 1 nM, at least 100 pM, at least 10 pM, or at least 1 pM, as determined by a method such as above-described.

In a particular embodiment, the present invention relates to a method for the diagnosis of prostate cancer, comprising the detection of the concentration of progastrin in a biological sample from a subject, wherein said biological sample is contacted with an anti-hPG antibody, or an antigen-binding fragment thereof.

The term "antibody" as used herein is intended to include polyclonal and monoclonal antibodies. An antibody (or "immunoglobulin") consists of a glycoprotein comprising at least two heavy (H) chains and two light (L) chains interconnected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed "complementarity determining regions" (CDR) or "hypervariable regions", which are primarily responsible for binding an epitope of an antigen, and which are interspersed with regions that are more conserved, termed framework regions (FR). Method for identifying the CDRs within light and heavy chains of an antibody and determining their sequence are well known to the skilled person. For the avoidance of doubt, in the absence of any indication in the text to the contrary, the expression CDRs means the hypervariable regions of the heavy and light chains of an antibody as defined by IMGT, wherein the IMGT unique numbering provides a standardized delimitation of the framework regions and of the complementary determining regions, CDR1-IMGT: 27 to 38, CDR2.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23

(1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system. Antibodies can be of different isotypes (namely IgA, IgD, IgE, IgG or IgM).

In a particular embodiment, said progastrin-binding antibody, or an antigen-binding fragment thereof, is selected from the group consisting of: polyclonal antibodies, monoclonal antibodies, chimeric antibodies, single chain antibodies, camelized antibodies, IgA1 antibodies, IgA2 antibodies, IgD antibodies, IgE antibodies, IgG1 antibodies, IgG2 antibodies, IgG3 antibodies, IgG4 antibodies and IgM antibodies.

A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal.

The term "monoclonal antibody" designates an antibody arising from a nearly homogeneous antibody population, wherein population comprises identical antibodies except for a few possible naturally-occurring mutations which can be found in minimal proportions. A monoclonal antibody arises from the growth of a single cell clone, such as a hybridoma, and is characterized by heavy chains of one class and subclass, and light chains of one type.

By the expression "antigen-binding fragment" of an antibody, it is intended to indicate any peptide, polypeptide, or protein retaining the ability to bind to the target (also generally referred to as antigen) of the said antibody, generally the same epitope, and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino acid residues, at least 70 contiguous amino acid residues, at least 80 contiguous amino acid residues, at least 90 contiguous amino acid residues, at least 100 contiguous amino acid residues, at least 125 contiguous amino acid residues, at least 150 contiguous amino acid residues, at least 175 contiguous amino acid residues, or at least 200 contiguous amino acid residues, of the amino acid sequence of the antibody.

In a particular embodiment, the said antigen-binding fragment comprises at least one CDR of the antibody from which it is derived. Still in a preferred embodiment, the said antigen binding fragment comprises 2, 3, 4 or 5 CDRs, more preferably the 6 CDRs of the antibody from which it is derived.

The "antigen-binding fragments" can be selected, without limitation, in the group consisting of Fv, scFv (sc for single chain), Fab, F(ab')2, Fab', scFv-Fc fragments or diabodies, or fusion proteins with disordered peptides such as XTEN (extended recombinant polypeptide) or PAS motifs, or any fragment of which the half-life time would be increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen-binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target.

In another particular embodiment, in a method for the diagnosis of prostate cancer according to the invention, a biological sample from a subject is contacted with an antibody binding to progastrin, wherein said antibody has been obtained by an immunization method known by a person skilled in the art, wherein using as an immunogen a peptide which amino acid sequence comprises the totality or a part of the amino-acid sequence of progastrin. More particularly, said immunogen comprises a peptide chosen among:

a peptide which amino acid sequence comprises, or consists of, the amino acid sequence of full length progastrin, and particularly full length human progastrin of SEQ ID NO:1, a peptide which amino acid sequence corresponds to a part of the amino acid sequence of progastrin, and particularly full length human progastrin of SEQ ID NO:1, a peptide which amino acid sequence corresponds to a part or to the whole amino acid sequence of the N-terminal part of progastrin, and in particular peptides comprising, or consisting of, the amino acid sequence: SWKPRSQQPDAPLG (SEQ ID NO:2), and a peptide which amino acid sequence corresponds to a part or to the whole amino acid sequence of the C-terminal part of progastrin, and in particular peptides comprising, or consisting of, the amino acid sequence: QGPWLEEEEEAYGWMDFGRRSAEDEN (SEQ ID NO:3), a peptide which amino acid sequence corresponds to a part of the amino acid sequence of the C-terminal part of progastrin, and in particular peptides comprising the amino acid sequence FGRRSAEDEN (SEQ ID NO:40) corresponding to amino acids 71-80 of progastrin The skilled person will realize that such immunization may be used to generate either polyclonal or monoclonal antibodies, as desired. Methods for obtaining each of these types of antibodies are well known in the art. The skilled person will thus easily select and implement a method for generating polyclonal and/or monoclonal antibodies against any given antigen.

Examples of monoclonal antibodies which were generated by using an immunogen comprising the amino-acid sequence "SWKPRSQQPDAPLG" (SEQ ID NO:2), corresponding to the amino acid sequence 1-14 of human progastrin (N-terminal extremity) include, but are not restricted to, monoclonal antibodies designated as: mAb3, mAb4, mAb16, and mAb19 and mAb20, as described in the following Table 1 to Table 4. Other monoclonal antibodies have been described, although it is not clear whether these antibodies actually bind progastrin (WO 2006/032980). Experimental results of epitope mapping show that mAb3, mAb4, mAb16, and mAb19 and mAb20 do specifically bind an epitope within said hPG N-terminal amino acid sequence. Polyclonal antibodies recognizing specifically an epitope within the N-terminus of progastrin represented by SEQ ID NO:2, have been described in the art (see e.g., WO 2011/083088).

TABLE 1

| Hybridoma deposit | mAb | Amino acid sequences | | SEQ ID No |
|---|---|---|---|---|
| 6B51311C10 | mAb3 | VH CDR 1 | GYIFTSYW | SEQ ID NO: 4 |
| | | VH CDR 2 | FYPGNSDS | SEQ ID NO: 5 |
| | | VH CDR 3 | TRRDSPQY | SEQ ID NO: 6 |
| | | VL CDR 1 | QSIVHSNGNTY | SEQ ID NO: 7 |
| | | VL CDR 2 | KVS | SEQ ID NO: 8 |
| | | VL CDR 3 | FQGSHVPFT | SEQ ID NO: 9 |
| | | mVH 3 | EVQLQQSGTVLARPGASVKMSCK ASGYIFTSYWVHWVKQRPGQGLE WIGGFYPGNSDSRYNQKFKGKAT LTAVTSASTAYMDLSSLTNEDSAV YFCTRRDSPQYWGQGTTLTVSS | SEQ ID NO: 41 |
| | | mVL 3 | DVLMTQTPLSLPVSLGDQASISCR SSQSIVHSNGNTYLEWYLQKPGQS PKLLIYKVSNRFSGVPDRFSGSGS GTDFTLKISRLEAEDLGVYYCFQG SHVPFTFGGGTKLEIK | SEQ ID NO: 42 |
| | | huVH 3 | QVQLVQSGAEVKKPGASVKVSCK ASGYIFTSYWVHWVRQAPGQRLE WMGGFYPGNSDSRYSQKFQGRV TITRDTSASTAYMELSSLRSEDTAV YYCTRRDSPQYWGQGTLVTVSS | SEQ ID NO: 53 |
| | | huVL 3 | DVVMTQSPLSLPVTLGQPASISCR SSQSIVHSNGNTYLEWFQQRPGQ SPRRLIYKVSNRFSGVPDRFSGSGS GTDFTLKISRVEAEDVGVYYCFQG SHVPFTFGGGTKVEIK | SEQ ID NO: 54 |

TABLE 2

| Hybridoma deposit | mAb | Amino acid sequences | | SEQ ID No |
|---|---|---|---|---|
| 20D2C3G2 | mAb4 | VH CDR 1 | GYTFSSW | SEQ ID NO: 10 |
| | | VH CDR 2 | FLPGSGST | SEQ ID NO: 11 |
| | | VH CDR 3 | ATDGNYDWFAY | SEQ ID NO: 12 |
| | | VL CDR 1 | QSLVHSSGVTY | SEQ ID NO: 13 |
| | | VL CDR 2 | KVS | SEQ ID NO: 14 |
| | | VL CDR 3 | SQSTHVPPT | SEQ ID NO: 15 |
| | | mVH 4 | QVQLQQSGAELMKPGASVKISCK ATGYTFSSSWIEWLKQRPGHGLE WIGEFLPGSGSTDYNEKFKGKATF TADTSSDTAYMLLSSLTSEDSAVY YCATDGNYDWFAYWGQGTLVTV SA | SEQ ID NO: 43 |

TABLE 2-continued

| Hybridoma deposit | mAb | Amino acid sequences | SEQ ID No |
|---|---|---|---|
| | mVL 4 | DLVMTQTPLSLPVSLGDQASISCR SSQSLVHSSGVTYLHWYLQKPGQ SPKLLIYKVSNRFSGVPDRFSGSGS GTDFTLKISRVEAEDLGVYFCSQS THVPPTFGSGTKLEIK | SEQ ID NO: 44 |
| | huVH 4 | QVQLVQSGAEVKKPGASVKVSCK ASGYTFSSSWMHWVRQAPGQGL EWMGIFLPGSGSTDYAQKFQGRV TMTRDTSTSTVYMELSSLRSEDTA VYYCATDGNYDWFAYWGQGTLV TVSS | SEQ ID NO: 55 |
| | huVL 4 | DIVMTQTPLSLSVTPGQPASISCKS SQSLVHSSGVTYLYWYLQKPGQS PQLLIYKVSNRFSGVPDRFSGSGS GTDFTLKISRVEAEDVGVYYCSQS THVPPTFGQGTKLEIK | SEQ ID NO: 56 |

TABLE 3

| Hybridoma deposit | mAb | Amino acid sequences | SEQ ID No |
|---|---|---|---|
| 1E9D9B6 | mAb16 VH CDR 1 | GYTFTSYY | SEQ ID NO: 16 |
| | VH CDR 2 | INPSNGGT | SEQ ID NO: 17 |
| | VH CDR 3 | TRGGYYPFDY | SEQ ID NO: 18 |
| | VL CDR 1 | QSLLDSDGKTY | SEQ ID NO: 19 |
| | VL CDR 2 | LVS | SEQ ID NO: 20 |
| | VL CDR 3 | WQGTHSPYT | SEQ ID NO: 21 |
| | mVH 16 | QVQLQQSGAELVKPGASVKLSCK ASGYTFTSYYMYWVKQRPGQGLE WIGEINPSNGGTNFNEKFKSKATL TVDKSSSTAYMQLSSLTSEDSAVY YCTRGGYYPFDYWGQGTTLTVSS | SEQ ID NO: 45 |
| | mVL 16 | DVVMTQTPLTLSVTIGRPASISCKS SQSLLDSDGKTYLYWLLQRPGQS PKRLIYLVSELDSGVPDRITGSGSG TDFTLKISRVEAEDLGVYYCWQG THSPYTFGGGTKLEIK | SEQ ID NO: 46 |
| | huVH 16a | QVQLVQSGAEVKKPGASVKVSCK ASGYTFTSYYMYWVRQAPGQGLE WMGIINPSNGGTSYAQKFQGRVT MTRDTSTSTVYMELSSLRSEDTAV YYCTRGGYYPFDYWGQGTTVTV SS | SEQ ID NO: 57 |
| | huVH 16b | QVQLVQSGAEVKKPGASVKVSCK ASGYTFTSYYMHWVRQAPGQGL EWMGIINPSNGGTSYAQKFQGRV TMTRDTSTSTVYMELSSLRSEDTA VYYCTRGGYYPFDYWGQGTTVT VSS | SEQ ID NO: 58 |
| | huVH 16c | QVQLVQSGAEVKKPGASVKVSCK ASGYTFTSYYMYWVRQAPGQGLE WMGEINPSNGGTNYAQKFQGRV TMTRDTSTSTVYMELSSLRSEDTA VYYCTRGGYYPFDYWGQGTTVT VSS | SEQ ID NO: 59 |
| | huVL 16a | DVVMTQSPLSLPVTLGQPASISCR SSQSLLDSDGKTYLYWFQQRPGQ SPRRLIYLVSNRDSGVPDRFSGSGS GTDFTLKISRVEAEDVGVYYCWQ GTHSPYTFGQGTKLEIK | SEQ ID NO: 60 |

TABLE 3-continued

| Hybridoma deposit | mAb | Amino acid sequences | | SEQ ID No |
|---|---|---|---|---|
| | | huVL 16b | DVVMTQSPLSLPVTLGQPASISCR SSQSLLDSDGKTYLNWFQQRPGQ SPRRLIYLVSNRDSGVPDRFSGSGS GTDFTLKISRVEAEDVGVYYCWQ GTHSPYTFGQGTKLEIK | SEQ ID NO: 61 |
| | | huVL 16c | DVVMTQSPLSLPVTLGQPASISCR SSQSLLDSDGKTYLYWFQQRPGQ SPRRLIYLVSERDSGVPDRFSGSGS GTDFTLKISRVEAEDVGVYYCWQ GTHSPYTFGQGTKLEIK | SEQ ID NO: 62 |

TABLE 4

| Hybridoma deposit | mAb | Amino acid sequences | | SEQ ID No |
|---|---|---|---|---|
| 1B3B4F11 | mAb19 | VH CDR 1 | GYSITSDYA | SEQ ID NO: 22 |
| | | VH CDR 2 | ISFSGYT | SEQ ID NO: 23 |
| | | VH CDR 3 | AREVNYGDSYHFDY | SEQ ID NO: 24 |
| | | VL CDR 1 | SQHRTYT | SEQ ID NO: 25 |
| | | VL CDR 2 | VKKDGSH | SEQ ID NO: 26 |
| | | VL CDR 3 | GVGDAIKGQSVFV | SEQ ID NO: 27 |
| | | mVH 19 | DVQLQESGPGLVKPSQSLSLTCTV TGYSITSDYAWNWIRQFPGNKLE WMGYISFSGYTSYNPSLKSRISVTR DTSRNQFFLQLTSVTTEDTAMC AREVNYGDSYHFDYWGQGTIVTV SS | SEQ ID NO: 47 |
| | | mVL 19 | QLALTQSSSASFSLGASAKLTCTLS SQHRTYTIEWYQQQSLKPPKYVM EVKKDGSHSTGHGIPDRFSGSSSG ADRYLSISNIQPEDEAIYICGVGDAI KGQSVFVFGGGTKVTVL | SEQ ID NO: 48 |
| | | huVH 19a | QVQLQESGPGLVKPSQTLSLTCT VSGYSITSDYAWNWIRQHPGKGL EWIGYISFSGYTYYNPSLKSRVTIS VDTSKNQFSLKLSSVTAADTAVYY CAREVNYGDSYHFDYWGQGTLV TVSS | SEQ ID NO: 63 |
| | | huVH 19b | QVQLQESGPGLVKPSQTLSLTCT VSGYSITSDYAWSWIRQHPGKGLE WIGYISFSGYTYYNPSLKSRVTISV DTSKNQFSLKLSSVTAADTAVYYC AREVNYGDSYHFDYWGQGTLVT VSS | SEQ ID NO: 64 |
| | | huVH 19c | QVQLQESGPGLVKPSQTLSLTCT VSGYSITSDYAWNWIRQHPGKGL EWIGYISFSGYTSYNPSLKSRVTIS VDTSKNQFSLKLSSVTAADTAVYY CAREVNYGDSYHFDYWGQGTLV TVSS | SEQ ID NO: 65 |
| | | huVL 19a | QLVLTQSPSASASLGASVKLTCTL SSQHRTYTIEWHQQQPEKGPRYL MKVKKDGSHSKGDGIPDRFSGSSS GAERYLTISSLQSEDEADYYCGVG DAIKGQSVFVFGGGTKVEIK | SEQ ID NO: 66 |
| | | huVL 19b | QLVLTQSPSASASLGASVKLTCTL SSQHRTYTIAWHQQQPEKGPRYL MKVKKDGSHSKGDGIPDRFSGSSS GAERYLTISSLQSEDEADYYCGVG DAIKGQSVFVFGGGTKVEIK | SEQ ID NO: 67 |

TABLE 4-continued

| Hybridoma deposit | mAb | Amino acid sequences | SEQ ID No |
|---|---|---|---|
| | huVL 19c | QLVLTQSPSASASLGASVKLTCTL SSQHRTYTIEWHQQQPEKGPRYL MEVKKDGSHSKGDGIPDRFSGSSS GAERYLTISSLQSEDEADYYCGVG DAIKGQSVFVFGGGTKVEIK | SEQ ID NO: 68 |

Examples of monoclonal antibodies that can be generated by using an immunogen comprising the amino-acid sequence "QGPWLEEEEEAYGWMDFGRRSAEDEN" (SEQ ID NO:3), (C-terminal part of progastrin) corresponding to the amino acid sequence 55-80 of human progastrin include, but are not restricted to antibodies designated as: mAb8 and mAb13 in the following Table 5 and 6. Experimental results of epitope mapping show that mAb13 do specifically bind an epitope within said hPG C-terminal amino acid sequence. Another example of a monoclonal antibody that can thus be generated by is the antibody Mab14, produced by hybridoma 2H9F4B7, described in WO 2011/083088. Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference 1-5158 (see WO 2017/114973).

TABLE 5

| Hybridoma deposit | mAb | | Amino acid sequences | SEQ ID No |
|---|---|---|---|---|
| 1C10D3B9 | mAb8 | VH CDR 1 | GFTFTTYA | SEQ ID NO: 28 |
| | | VH CDR 2 | ISSGGM | SEQ ID NO: 29 |
| | | VH CDR 3 | ATQGNYSLDF | SEQ ID NO: 30 |
| | | VL CDR 1 | KSLRHTKGITF | SEQ ID NO: 31 |
| | | VL CDR 2 | QMS | SEQ ID NO: 32 |
| | | VL CDR 3 | AQNLELPLT | SEQ ID NO: 33 |
| | | mVH 8 | EVQLVESGGGLVKPGGSLRLSC AASGFTFTTYAMSWVRQAPGK GLEWVATISSGGTYTYYADSVK GRFTISRDNAKNSLYLQMNSLRA EDTAVYYCATQGNYSLDFWGQ GTTVTVSS | SEQ ID NO: 49 |
| | | mVL 8 | DIVMTQSPLSLPVTPGEPASISCR SSKSLRHTKGITFLYWYLQKPGQ SPQLLIYQMSNLASGVPDRFSSS GSGTDFTLKISRVEAEDVGVYYC AQNLELPLTFGGGTKVEIK | SEQ ID NO: 50 |
| | | VH hZ8CV1 | EVQLVESGGGLVKPGGSLRLSC AASGFTFTTYAMSWVRQAPGK GLEWVSSISSGGTYTYYADSVKG RFTISRDNAKNSLYLQMNSLRAE DTAVYYCATQGNYSLDFWGQG TTVTVSS | SEQ ID NO: 69 |
| | | VL hZ8CV1 | DIVMTQSPLSLPVTPGEPASISCR SSKSLRHTKGITFLYWYLQKPGQ SPQLLIYQMSNRASGVPDRFSGS GSGTDFTLKISRVEAEDVGVYYC AQNLELPLTFGGGTKVEIK | SEQ ID NO: 70 |
| | | VH hZ8CV2 | EVQLVESGGGLVKPGGSLRLSC AASGFTFTTYAMSWVRQAPGK GLEWVATISSGGTYTYYADSVK GRFTISRDNAKNSLYLQMNSLRA EDTAVYYCATQGNYSLDFWGQ GTTVTVSS | SEQ ID NO: 71 |
| | | VL hZ8CV2 | DIVMTQSPLSLPVTPGEPASISCR SSKSLRHTKGITFLYWYLQKPGQ SPQLLIYQMSNLASGVPDRFSSS GSGTDFTLKISRVEAEDVGVYYC AQNLELPLTFGGGTKVEIK | SEQ ID NO: 72 |

TABLE 5-continued

| Hybridoma deposit | mAb | Amino acid sequences | SEQ ID No |
|---|---|---|---|
| | CH hZ8CV2 | EVQLVESGGGLVKPGGSLRLSCAASGFTFTTYAMSWVRQAPGKGLEWVATISSGGTYTYYADSVKGRFTISRDNAKNSLYLQMNSLRAEDTAVYYCATQGNYSLDFWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | SEQ ID NO: 73 |
| | CL hZ8CV2 | DIVMTQSPLSLPVTPGEPASISCRSSKSLRHTKGITFLYWYLQKPGQSPQLLIYQMSNLASGVPDRFSSSGSGTDFTLKISRVEAEDVGVYYCAQNLELPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC | SEQ ID NO: 74 |

TABLE 6

| Hybridoma deposit | mAb | Amino acid sequences | SEQ ID No |
|---|---|---|---|
| 2C6C3C7 | mAb13 VH CDR 1 | GFIFSSYG | SEQ ID NO: 34 |
| | VH CDR 2 | INTFGDRT | SEQ ID NO: 35 |
| | VH CDR 3 | ARGTGTY | SEQ ID NO: 36 |
| | VL CDR 1 | QSLLDSDGKTY | SEQ ID NO: 37 |
| | VL CDR 2 | LVS | SEQ ID NO: 38 |
| | VL CDR 3 | WQGTHFPQT | SEQ ID NO: 39 |
| | mVH 13 | EVQLVESGGGLVQPGGSLKLSCAASGFIFSSYGMSWVRQSPDRRLELVASINTFGDRTYYPDSVKGRFTISRDNAKNTLYLQMTSLKSEDTAIYYCARGTGTYWGQGTTLTVSS | SEQ ID NO: 51 |
| | mVL 13 | DVVLTQTPLTLSVTIGQPASISCKSSQSLLDSDGKTYLNWLLQRPGQSPKRLIYLVSKLDSGVPDRFTGSGSGTDFTLKISRVEAEDLGVYYCWQGTHFPQTFGGGTKLEIK | SEQ ID NO: 52 |
| | huVH 13a | EVQLVESGGGLVQPGGSLRLSCAASGFIFSSYGMSWVRQAPGKGLEWVANINTFGDRTYYVDSVKGRFTISRDNAKNSLYLQMNSLRAEDTAVYYCARGTGTYWGQGTLVTVSS | SEQ ID NO: 75 |

TABLE 6-continued

| Hybridoma deposit | mAb | Amino acid sequences | | SEQ ID No |
|---|---|---|---|---|
| | huVH 13b | EVQLVESGGGLVQPGGSLRLSC AASGFIFSSYGMSWVRQAPGKG LEWVASINTFGDRTYYVDSVKG RFTISRDNAKNSLYLQMNSLRAE DTAVYYCARGTGTYWGQGTLV TVSS | | SEQ ID NO: 76 |
| | huVL 13a | DVVMTQSPLSLPVTLGQPASISC RSSQSLLDSDGKTYLNWFQQRP GQSPRRLIYLVSNRDSGVPDRFS GSGSGTDFTLKISRVEAEDVGVY YCWQGTHFPQTFGGGTKVEIK | | SEQ ID NO: 77 |
| | huVL 13b | DVVMTQSPLSLPVTLGQPASISC RSSQSLLDSDGKTYLNWFQQRP GQSPRRLIYLVSKRDSGVPDRFS GSGSGTDFTLKISRVEAEDVGVY YCWQGTHFPQTFGGGTKVEIK | | SEQ ID NO: 78 |

Other examples include anti-hPG monoclonal and/or polyclonal antibodies generated by using an immunogen comprising an amino acid sequence of SEQ ID NO:40.

In a more particular embodiment, in a method according to the invention said biological sample is contacted with an anti-hPG antibody or antigen-binding fragment thereof, wherein said anti-hPG antibody is chosen among N-terminal anti-hPG antibodies and C-terminal anti-hPG antibodies.

The terms "N-terminal anti-hPG antibodies" and "C-terminal anti-hPG antibodies" designate antibodies binding to an epitope comprising amino acids located in the N-terminal part of hPG or to an epitope comprising amino acids located in the C-terminal part of hPG, respectively. Preferably, the term "N-terminal anti-hPG antibodies" refers to antibodies binding to an epitope located in a domain of progastrin whose sequence is represented by SEQ ID NO:2. In another preferred embodiment, the term "C-terminal anti-hPG antibodies" refers to antibodies binding to an epitope located in a domain of progastrin whose sequence is represented by SEQ ID NO:3.

The term "epitope" refers to a region of an antigen that is bound by an antibody. Epitopes may be defined as structural or functional. Functional epitopes are generally a subset of the structural epitopes and have those amino acids that directly contribute to the affinity of the interaction. Epitopes may also be conformational. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. The determination of the epitope bound by an antibody may be performed by any epitope mapping technique, known by a man skilled in the art. An epitope may comprise different amino acids which located sequentially within the amino acid sequence of a protein. An epitope may also comprise amino acids which are not located sequentially within the amino acid sequence of a protein.

In a particular embodiment, said antibody is a monoclonal antibody selected in the group consisting of:

A monoclonal antibody comprising a heavy chain comprising at least one, preferentially at least two, preferentially three, of CDR-H1, CDR-H2 and CDR-H3 of amino acid sequences SEQ ID NO:4, 5 and 6, respectively, or sequences with at least 80%, preferably 85%, 90%, 95% and 98% identity after optimal alignment with sequences SEQ ID NO:4, 5 and 6, respectively, and a light chain comprising at least one, preferentially at least two, preferentially three, of CDR-L1, CDR-L2 and CDR-L3 of amino acid sequences SEQ ID NO:7, 8 and 9, respectively, or sequences with at least 80%, preferably 85%, 90%, 95% and 98% identity after optimal alignment with sequences SEQ ID NO:7, 8 and 9, respectively, A monoclonal antibody comprising a heavy chain comprising at least one, preferentially at least two, preferentially three, of CDR-H1, CDR-H2 and CDR-H3 of amino acid sequences SEQ ID NO:10, 11 and 12, respectively, or sequences with at least 80%, preferably 85%, 90%, 95% and 98% identity after optimal alignment with sequences SEQ ID NO:10, 11 and 12, respectively, and a light chain comprising at least one, preferentially at least two, preferentially three, of CDR-L1, CDR-L2 and CDR-L3 of amino acid sequences SEQ ID NO:13, 14 and 15, respectively, or sequences with at least 80%, preferably 85%, 90%, 95% and 98% identity after optimal alignment with sequences SEQ ID NO:13, 14 and 15, respectively, A monoclonal antibody comprising a heavy chain comprising at least one, preferentially at least two, preferentially three, of CDR-H1, CDR-H2 and CDR-H3 of amino acid sequences SEQ ID NO:16, 17 and 18, respectively, or sequences with at least 80%, preferably 85%, 90%, 95% and 98% identity after optimal alignment with sequences SEQ ID NO:16, 17 and 18, respectively, and a light chain comprising at least one, preferentially at least two, preferentially three, of CDR-L1, CDR-L2 and CDR-L3 of amino acid sequences SEQ ID NO:19, 20 and 21, respectively, or sequences with at least 80%, preferably 85%, 90%, 95% and 98% identity after optimal alignment with sequences SEQ ID NO:19, 20 and 21, respectively, A monoclonal antibody comprising a heavy chain comprising at least one, preferentially at least two, preferentially three, of CDR-H1, CDR-H2 and CDR-H3 of amino acid sequences SEQ ID NO:22, 23 and 24, respectively, or sequences with at least 80%, preferably 85%, 90%, 95% and 98% identity after optimal alignment with sequences SEQ ID NO:22, 23 and 24, respectively, and a light chain comprising at least one, preferentially at least two, preferentially three, of CDR- L1, CDR-L2 and CDR-L3 of amino acid sequences SEQ ID NO:25, 26 and 27, respectively, or sequences with at least 80%, preferably 85%, 90%, 95% and 98% identity after optimal alignment with sequences SEQ ID NO:25, 26 and 27, respectively, A monoclonal antibody comprising a heavy chain comprising at least one, preferentially at least two, preferentially at least three, of CDR-H1, CDR-H2 and CDR-H3 of amino acid sequences SEQ ID NO:28, 29 and 30, respectively, or sequences with at least 80%, preferably 85%, 90%, 95% and 98% identity after optimal alignment with sequences SEQ ID NO:28, 29 and 30, respectively, and a light chain comprising at least one, preferentially at least two, preferentially three, of CDR-L1, CDR-L2 and CDR-L3 of amino acid sequences SEQ ID NO:31, 32 and 33, respectively, or sequences with at least 80%, preferably 85%, 90%, 95% and 98% identity after optimal alignment with sequences SEQ ID NO:31, 32 and 33, respectively, and A monoclonal antibody comprising a heavy chain comprising at least one, preferentially at least two, preferentially three, of CDR-H1, CDR-H2 and CDR-H3 of amino acid sequences SEQ ID NO:34, 35 and 36, respectively, or sequences with at least 80%, preferably 85%, 90%, 95% and 98% identity after optimal alignment with sequences SEQ ID NO:34, 35 and 36, respectively, and a light chain comprising at least one, preferentially at least two, preferentially three, of CDR-L1, CDR-L2 and CDR-L3 of amino acid sequences SEQ ID NO:37, 38 and 39, respectively, or sequences with at least 80%, preferably 85%, 90%, 95% and 98% identity after optimal alignment with sequences SEQ ID NO:37, 38 and 39, respectively.

In the sense of the present invention, the "percentage identity" or "% identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of methods known by a man skilled in the art.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antibodies likely to be generated.

In a more particular embodiment, said antibody is a monoclonal antibody selected in the group consisting of:

A monoclonal antibody comprising a heavy chain of amino acid sequence SEQ ID NO:41 and a light chain of amino acid sequence SEQ ID NO:42;

A monoclonal antibody comprising a heavy chain of amino acid sequence SEQ ID NO:43 and a light chain of amino acid sequence SEQ ID NO:44;

A monoclonal antibody comprising a heavy chain of amino acid sequence SEQ ID NO:45 and a light chain of amino acid sequence SEQ ID NO:46;

A monoclonal antibody comprising a heavy chain of amino acid sequence SEQ ID NO:47 and a light chain of amino acid sequence SEQ ID NO:48;

A monoclonal antibody comprising a heavy chain of amino acid sequence SEQ ID NO:49 and a light chain of amino acid sequence SEQ ID NO:50; and A monoclonal antibody comprising a heavy chain of amino acid sequence SEQ ID NO:51 and a light chain of amino acid sequence SEQ ID NO:52.

In another particular embodiment, the antibody used in the method of the invention is a humanised antibody.

As used herein, the expression "humanized antibody" means an antibody that contains CDR regions derived from an antibody of nonhuman origin, the other parts of the antibody molecule being derived from one or several human antibodies. In addition, some of the skeleton segment residues (called FR for framework) can be modified to preserve binding affinity, according to techniques known by a man skilled in the art (Jones et al., Nature, 321:522-525, 1986). The goal of humanisation is a reduction in the immunogenicity of a xenogenic antibody, such as a murine antibody, for introduction into a human, while maintaining the full antigen binding affinity and specificity of the antibody.

The humanized antibodies of the invention or fragments of same can be prepared by techniques known to a person skilled in the art (such as, for example, those described in the documents Singer et al., J. Immun., 150:2844-2857, 1992). Such humanized antibodies are preferred for their use in methods involving in vitro diagnoses or preventive and/or therapeutic treatment in vivo. Other humanization techniques are also known to the person skilled in the art. Indeed, Antibodies can be humanized using a variety of techniques including CDR-grafting (EP 0 451 261; EP 0 682 040; EP 0 939 127; EP 0 566 647; U.S. Pat. Nos. 5,530,101; 6,180,370; 5,585,089; 5,693,761; 5,639,641; 6,054,297; 5,886,152; and 5,877,293), veneering or resurfacing (EP 0 592 106; EP 0 519 596; Padlan E. A., 1991, Molecular Immunology 28(4/5): 489-498; Studnicka G. M. et al., 1994, Protein Engineering 7(6): 805-814; Roguska M. A. et al., 1994, Proc. Natl. Acad. ScL U.S.A., 91:969-973), and chain shuffling (U.S. Pat. No. 5,565,332). Human antibodies can be made by a variety of methods known in the art including phage display methods. See also U.S. Pat. Nos. 4,444,887, 4,716,111, 5,545,806, and 5,814,318; and international patent application publication numbers WO 98/46645, WO 98/50433, WO 98/24893, WO 98/16654, WO 96/34096, WO 96/33735, and WO 91/10741.

In a more particular embodiment, said antibody is a humanized antibody selected in the group consisting of:

A humanized antibody comprising a heavy chain comprising at least one, preferentially at least two, preferentially three, of CDR-H1, CDR-H2 and CDR-H3 of amino acid sequences SEQ ID NO:4, 5 and 6, respectively, or sequences with at least 80%, preferably 85%, 90%, 95% and 98% identity after optimal alignment with sequences SEQ ID NO:4, 5 and 6, respectively, and a light chain comprising at least one, preferentially at least two, preferentially three, of CDR-L1, CDR-L2 and CDR-L3 of amino acid sequences SEQ ID NO:7, 8 and 9, respectively, or sequences with at least 80%, preferably 85%, 90%, 95% and 98% identity after optimal alignment with sequences SEQ ID NO:7, 8 and 9, respectively, A humanized antibody comprising a heavy chain comprising at least one, preferentially at least two, preferentially three, of CDR-H1, CDR-H2 and CDR-H3 of amino acid sequences SEQ ID NO:10, 11 and 12, respectively, or sequences with at least 80%, preferably 85%, 90%, 95% and 98% identity after optimal alignment with sequences SEQ ID NO:10, 11 and 12, respectively, and a light chain comprising at least one, preferentially at least two, preferentially three, of CDR-L1, CDR-L2 and CDR-L3 of amino acid sequences SEQ ID NO:13, 14 and 15, respectively, or sequences with at least 80%, preferably 85%, 90%, 95% and 98% identity after optimal alignment with sequences SEQ ID NO:13, 14 and 15, respectively, A humanized antibody comprising a heavy chain comprising at least one, preferentially at least two, preferentially three, of CDR-H1, CDR-H2 and CDR-H3 of amino acid sequences SEQ ID NO:16, 17 and 18, respectively, or sequences with at least 80%, preferably 85%, 90%, 95% and 98% identity after optimal alignment with sequences SEQ ID NO:16, 17 and 18, respectively, and a light chain comprising at least one, preferentially at least two, preferentially three, of CDR-L1, CDR-L2 and CDR-L3 of amino acid sequences SEQ ID NO:19, 20 and 21, respectively, or sequences with at least 80%, preferably 85%, 90%, 95% and 98% identity after optimal alignment with sequences SEQ ID NO:19, 20 and 21, respectively, A humanized antibody comprising a heavy chain comprising at least one, preferentially at least two, preferentially three, of CDR-H1, CDR-H2 and CDR-H3 of amino acid sequences SEQ ID NO:22, 23 and 24, respectively, or sequences with at least 80%, preferably 85%, 90%, 95% and 98% identity after optimal alignment with sequences SEQ ID NO:22, 23 and 24, respectively, and a light chain comprising at least one, preferentially at least two, preferentially three, of CDR-L1, CDR-L2 and CDR-L3 of amino acid sequences SEQ ID NO:25, 26 and 27, respectively, or sequences with at least 80%, preferably 85%, 90%, 95% and 98% identity after optimal alignment with sequences SEQ ID NO:25, 26 and 27, respectively, A humanized antibody comprising a heavy chain comprising at least one, preferentially at least two, preferentially three, of CDR-H1, CDR-H2 and CDR-H3 of amino acid sequences SEQ ID NO:28, 29 and 30, respectively, or sequences with at least 80%, preferably 85%, 90%, 95% and 98% identity after optimal alignment with sequences SEQ ID NO:28, 29 and 30, respectively, and a light chain comprising at least one, preferentially at least two, preferentially three, of CDR-L1, CDR-L2 and CDR-L3 of amino acid sequences SEQ ID NO:31, 32 and 33, respectively, or sequences with at least 80%, preferably 85%, 90%, 95% and 98% identity after optimal alignment with sequences SEQ ID NO:31, 32 and 33, respectively, and A humanized antibody comprising a heavy chain comprising at least one, preferentially at least two, preferentially three, of CDR-H1, CDR-H2 and CDR-H3 of amino acid sequences SEQ ID NO:34, 35 and 36, respectively, or sequences with at least 80%, preferably 85%, 90%, 95% and 98% identity after optimal alignment with sequences SEQ ID NO:34, 35 and 36, respectively, and a light chain comprising at least one, preferentially at least two, preferentially three, of CDR-L1, CDR-L2 and CDR-L3 of amino acid sequences SEQ ID NO:37, 38 and 39, respectively, or sequences with at least 80%, preferably 85%, 90%, 95% and 98% identity after optimal alignment with sequences SEQ ID NO:37, 38 and 39, respectively, wherein said antibody also comprises constant regions of the light-chain and the heavy-chain derived from a human antibody.

In another more particular embodiment, said antibody is a humanized antibody selected in the group consisting of:

A humanized antibody comprising a heavy chain variable region of amino acid sequence SEQ ID NO:53, and a light chain variable region of amino acid sequence SEQ ID NO:54;

A humanized antibody comprising a heavy chain variable region of amino acid sequence SEQ ID NO:55, and a light chain variable region of amino acid sequence SEQ ID NO:56;

A humanized antibody comprising a heavy chain variable region of amino acid sequence selected between SEQ ID NO:57, 58, and 59, and a light chain variable region of amino acid sequence selected between SEQ ID NO:60, 61, and 62;

A humanized antibody comprising a heavy chain variable region of amino acid sequence selected between SEQ ID NO:63, 64, and 65, and a light chain variable region of amino acid sequence selected between SEQ ID NO:66, 67, and 68;

A humanized antibody comprising a heavy chain variable region of amino acid sequence selected between SEQ ID NO:69 and 71, and a light chain variable region of amino acid sequence selected between SEQ ID NO:70 and 72; and A humanized antibody comprising a heavy chain variable region of amino acid sequence selected between SEQ ID NO:75 and 76, and a light chain variable region of amino acid sequence selected between SEQ ID NO:77 and 78;

wherein said antibody also comprises constant regions of the light-chain and the heavy-chain derived from a human antibody.

In a first embodiment, a method according to the invention comprises contacting a biological sample with an anti-hPG antibody binding to an epitope of hPG, wherein said epitope is located within the C-terminal part of hPG or to an epitope located within the N-terminal part of hPG.

In a more specific embodiment, a method according to the invention comprises contacting a biological sample with an anti-hPG antibody binding to an epitope of hPG, wherein said epitope includes an amino acid sequence corresponding to an amino acid sequence of the N-terminal part of progastrin chosen among an amino acid sequence corresponding to amino acids 10 to 14 of hPG, amino acids 9 to 14 of hPG, amino acids 4 to 10 of hPG, amino acids 2 to 10 of hPG and amino acids 2 to 14 of hPG, wherein the amino acid sequence of hPG is SEQ ID NO:1.

In a more specific embodiment, a method according to the invention comprises contacting a biological sample with an anti-hPG antibody binding to an epitope of hPG, wherein said epitope includes an amino acid sequence corresponding to an amino acid sequence of the C-terminal part of progastrin, chosen among an amino acid sequence corresponding to amino acids 71 to 74 of hPG, amino acids 69 to 73 of hPG, amino acids 71 to 80 of hPG (SEQ ID NO:40), amino acids 76 to 80 of hPG, and amino acids 67 to 74 of hPG, wherein the amino acid sequence of hPG is SEQ ID NO:1.

In a first embodiment, a composition according to the invention comprises an antibody recognizing an epitope including an amino acid sequence corresponding to an amino acid sequence of progastrin.

In a more specific embodiment, a composition according to the invention comprises an antibody recognizing an epitope of progastrin wherein said epitope includes an amino acid sequence corresponding to an amino acid sequence of the N-terminal part of progastrin, wherein said amino acid sequence may include residues 10 to 14 of hPG, residues 9 to 14 of hPG, residues 4 to 10 of hPG, residues 2 to 10 of hPG or residues 2 to 14 of hPG, wherein the amino acid sequence of hPG is SEQ ID NO:1.

In a more specific embodiment, a composition according to the invention comprises an antibody recognizing an epitope of progastrin wherein said epitope includes an amino acid sequence corresponding to an amino acid sequence of the C-terminal part of progastrin, wherein said amino acid sequence may include residues 71 to 74 of hPG, residues 69 to 73 of hPG, residues 71 to 80 of hPG (SEQ ID NO:40), residues 76 to 80 of hPG, or residues 67 to 74 of hPG, wherein the amino acid sequence of hPG is SEQ ID NO1.

In a particular embodiment of a method for the in vitro diagnosis of prostate cancer according to the invention, said method comprises a step of contacting a biological sample from a subject with a first molecule which binds to a first part of progastrin and with a second molecule which binds to a second part of progastrin. In a more particular embodiment, wherein said progastrin-binding molecule is an antibody, a biological sample from a subject is contacted with an antibody which binds to a first epitope of progastrin and with a second antibody which binds to a second epitope of progastrin.

In a particular embodiment of the method of the invention, said method comprises a step of contacting a biological sample from a subject with a first agent which binds to a first part of progastrin and with a second agent which binds to a second part of progastrin. In a more particular embodiment, wherein said progastrin-binding molecule is an antibody, a biological sample from a subject is contacted with an antibody which binds to a first epitope of progastrin and with a second antibody which binds to a second epitope of progastrin.

According to a preferred embodiment, said first antibody is bound to an insoluble or partly soluble carrier. Binding of progastrin by said first antibody results in capture of progastrin from said biological sample. Preferably, said first antibody is an antibody binding to an epitope of hPG, wherein said epitope includes an amino acid sequence corresponding to an amino acid sequence of the C-terminal part of progastrin, as described above. More preferably, said first antibody is monoclonal antibody Mab14, produced by hybridoma 2H9F4B7, described in WO 2011/083088. Hybridoma 2H9F4B7 was deposited under the Budapest Treaty at the CNCM, Institut Pasteur, 25-28 rue du Docteur Roux, 75724 Paris CEDEX 15, France, on 27 Dec. 2016, under reference 1-5158 (see WO 2017/114973).

According to another preferred embodiment, said second antibody is labelled with a detectable moiety, as described below. Binding of progastrin by second antibody enables the detection of the progastrin molecules which were present in the biological sample. Further, binding of progastrin by second antibody enables the quantification of the progastrin molecules which were present in the biological sample. Preferably, said second antibody is an antibody binding to an epitope of hPG, wherein said epitope includes an amino acid sequence corresponding to an amino acid sequence of the N-terminal part of progastrin, as described above. More preferably, said N-terminal antibody is a polyclonal antibody, as described above. Alternatively, it is also possible to use a monoclonal antibody biding an epitope within the N-terminus of progastrin, such as e.g. the N-terminus monoclonal antibodies described above, notably a monoclonal antibody comprising a heavy chain comprising CDR-H1, CDR-H2 and CDR-H3 of amino acid sequences SEQ ID NO:16, 17 and 18, respectively, and a light chain comprising CDR-L1, CDR-L2 and CDR-L3 of amino acid sequences SEQ ID NO:19, 20 and 21.

In a particularly preferred embodiment, the first antibody is bound to an insoluble or partly soluble carrier and the second antibody is labelled with a detectable moiety.

In a preferred embodiment, the method of the present invention for the diagnosis of prostate cancer comprises the detection of progastrin in a biological sample from a human subject.

In a more preferred embodiment, the method of the present invention for the diagnosis of prostate cancer comprises the determination of the concentration of progastrin in a biological sample from a human subject.

In another particular embodiment, the method of the present invention for the diagnosis of prostate cancer comprises the detection of the concentration of progastrin in a biological sample from a human subject, wherein said biological sample is selected from blood, serum and plasma.

In a further preferred embodiment, the method of the present invention comprises contacting a sample from said subject with an anti-hPG antibody as described above, wherein the binding of said anti-hPG antibody in the sample indicates the presence of prostate cancer in said subject.

In a more particular embodiment, the method of the present invention comprises contacting a sample from said subject with an anti-hPG antibody as described above, wherein a concentration of progastrin superior to 10 pM in said plasma is indicative of the presence of prostate cancer in said subject.

More preferably, the method of the present invention comprises contacting a sample from said subject with an anti-hPG antibody as described above, wherein a concentration of progastrin superior to 10 pM, 20 pM, 30 pM or 40 pM in said sample is indicative of the presence of prostate cancer in said subject.

Still more preferably, the method of the present invention comprises contacting a sample from said subject with an anti-hPG antibody as described above, wherein a concentration of progastrin superior to 10 pM, preferably to 20 pM, more preferably to 30 pM, still more preferably to 40 pM, even more preferably to 50 pM in said sample is indicative of the presence of metastasized prostate cancer in said subject The present invention also relates to methods for monitoring the efficacy of a treatment for prostate cancer in a patient, such as chemotherapy, biological therapy, immunotherapy or antibody therapy, by determining the concentration of progastrin in a first sample, such as a bodily fluid or biopsy of prostate cancer, obtained from a patient before treatment for prostate cancer, and then comparing the concentration of progastrin in the first sample to that in a second sample obtained from the same patient after treatment, where a reduction in the concentration of progastrin in said second sample compared to said first sample indicates that the treatment was effective.

In a particular embodiment, a method according to the invention comprises comparing the concentration of progastrin in a biological sample obtained from a patient with a predetermined value of concentration of progastrin in the sample, in a more particular embodiment, said predetermined value is chosen among: an mean, or average, of sample values based on the mean, or average, determination of the value in a population free of prostate cancer, a progastrin concentration value obtained when the patient was known to be free of prostate cancer.

In a particular embodiment, a method according to the invention for the in vitro diagnosis of prostate cancer comprises the determination of progastrin concentration in a sample from said patient and a second diagnosis test of prostate cancer. In a more particular embodiment, a method according to the invention for the in vitro diagnosis of prostate cancer comprises the determination of progastrin concentration in a sample from said patient and a second diagnosis test of prostate cancer, wherein said second diagnosis test comprises the detection of a particular biomarker, such as e.g., PSA, kallikreins, PCa antigen 3 (PCa3), TMPRSS2-ERG, SChLAP1, three exosomes genes (ERG, PCA3, SPDEF), a urinary two gene combination (HOXC6 and DLX1), as well as any other prostate cancer biomarker known to the skilled person (see e.g., McGrath et al., Prostate Int. 2016, 4(4): 130-135).

In a particular embodiment of the invention, a method according to the present invention comprises the determination of the level of progastrin over time in samples from a patient who has been or is being treated for prostate cancer.

The characteristics of the embodiments of the invention will become further apparent from the following detailed description of examples below.

EXAMPLES

Example 1: Detection of Plasmatic Progastrin Concentration Using Polyclonal Antibodies Plasma progastrin levels were quantified by ELISA through the use of two specific anti-progastrin antibodies: capture antibodies are coated on the wells of the plate, whereas revelation antibodies are used to detect progastrin and mediates revelation of the signal.

In the present example, quantification is based on the ELISA method which allows, through the use of a substrate whose reaction emits light, to assign a value proportional to the luminescence amount of antibodies bound to the antigen retained by capture antibodies.

Material

Reagents and apparatus are listed in Table 7:

TABLE 7

| Désignation | Provider | Référence |
| --- | --- | --- |
| Plates MaxiSORP white Nunc, 96 wells | Dutscher | # 055221 |
| Sodium Carbonate/Bicarbonate | Sigma | # 21851 |
| DPBS 1X | Lonza | # P04-36500 |
| Tween-20 | Biosolve | # 20452335 |
| BSA | Euronnedex | # 04-100-810-C |
| Streptavidin-HRP | Pierce (Thermo) | # 21130 |
| SuperSignal ELISA Femto Maximum Sensitivity Substrate | Pierce (Thermo) | # 37074 |
| Anti-ProGastrin Polyclonal Antibody | Eurogentec | / |

Polyclonal antibodies were obtained by immunizing a rabbit with N-terminal progastrin (SEQ ID NO:2) or with C-terminal progastrin corresponding to amino acids 71 to 80 of hPG and having the sequence FGRRSAEDEN (SEQ ID NO:40), according to standard protocols.

The binding characteristics of polyclonal antibodies against progastrin used in this assay are the following: absence of binding to G34-Gly, G34, G17-Gly, G17, binding to full length progastrin.

96 wells plates are coated by preparing a solution of carbonate—sodium bicarbonate, 50 mM pH 9.6 by dissolving the contents of one capsule in 100 ml of MilliQ water. A solution of capture antibody (3 µg/ml), corresponding to polyclonal antibodies obtained by using the C-terminal of progastrin FGRRSAEDEN (SEQ ID NO:40) is prepared in carbonate buffer. 100 microliters of antibodies solution is added to each well and incubated at 4° C. for 16 hours (1 night). Plates are then blocked by eliminating the antibodies solution and wash 3 times with 300 µl 1×PBS/0.1% Tween-20, then adding 200 µl of blocking buffer (1×PBS/0.1% Tween-20/0.1% BSA) per well, and incubated 2 hours at 22° C. Blocking buffer is then eliminated, wells are washed 3 times with 300 µl 1×PBS/0.1% Tween-20.

Plasma dilution is performed as follows: The plasma is used pure, diluted 1/2, 1/5 and 1/10. Dilutions are prepared from pure plasma in 1×PBS/0.1% Tween 20/0.1% BSA.

For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate.

Ranges of progastrin concentrations were prepared as follows:

Solution A: Pre-dilution 1/10, 2 µl of stock+18 µl of the buffer
Solution B: Pre-dilution 1/100, 10 µl of A+90 µl of the buffer
Solution C: Pre-dilution 1/1000, 10 µl of B+90 µl of the buffer
Solution D: 500 pM, 5.55 µl of C+494.5 µl of the diluent
Solution E: 250 pM, 250 µl of D+250 µl of the diluent
Solution F: 100 pM, 200 µl of E+300 µl of the diluent
Solution G: 50 pM, 250 µl of F+250 µl of the diluent
Solution H: 25 pM, 200 µl of G+200 µl of the diluent
Solution I: 10 pM, 100 µl of H+150 µl of the diluent The range of recombinant PG is linear and can therefore be more or less extensive according to the antibody used.

For the preparation of test samples, approximately 500 µl of each sample are set aside and stored until analysis (and confirmation if necessary) of the results. 100 µl of each point of the range and/or plasmas are assayed pure, diluted to 1/2, 1/5 and 1/10, and incubated for 2 hours at 22° C. on the plates.

For the revelation of the test, the plates are washed 3 times with 300 µl 1×PBS/0.1% Tween-20. A solution of the polyclonal rabbit anti-progastrin antibody, wherein said antibodies have been obtained by using the N-terminal part of progastrin as an immunogen, coupled to biotin to 0.5 µg/ml, is prepared by dilution in 1×PBS/0.1% Tween-20/0.1% BSA. 100 µl of this solution is added to each well. Incubation takes place for 1 hour at 22° C. The revelation with streptavidin-HRP is performed by removing detection antibody and wash 3 times with 300 µl 1×PBS/0.1% Tween-20, then preparing a solution of Streptavidin-HRP at 20 ng/ml diluted in 1×PBS/0.1% Tween-20/0.1% BSA, wherein 100 Add 100 µl of this solution is added to each well, before incubation for 1 hour at 22° C.

The detection consists of eliminating streptavidin-HRP and wash 3 times with 300 µl 1×PBS/0.1% Tween-20, then adding 100 µl of chemiluminescent substrate solution per well. The substrate solution is prepared by mixing equal volumes of the two solutions SuperSignal ELISA Femto kit, 20 ml+20 ml, 30 minutes before use and stored at room temperature in the dark. Luminescence is read after 5 minutes incubation at room temperature in the dark.

For each condition, the test is performed in triplicate and the results of the ranges will be presented as a graph showing the change in luminescence depending on the progastrin concentration. For each plasma dilution, the concentration of progastrin is determined using the equation of the linear regression line of the corresponding range (range 1/10th for a sample diluted to 1/10th).

Methods and Results

The median plasmatic concentration of progastrin is 0 pM in control patients, whereas a significant plasmatic concentration of progastrin can be detected in patients having prostate cancer (n=103). Thus, patients with prostate cancer have higher levels of progastrin in their plasma compared to healthy control individuals.

Example 2: Detection of Progastrin Concentration Using Monoclonal Anti-Progastrin Antibodies The wells of Nunc MaxiSORP 96-well plates are coated with a first progastrin-specific antibody as follows. Anti-progastrin monoclonal antibodies specific for the carboxy-terminal region of progastrin are diluted to a concentration of 3 µg/ml in a solution of 50 mM, pH 9.6 sodium carbonate/bicarbonate buffer in MilliQ water.

A total of 100 µl of the antibody solution is then added to each well of the 96-well plates, and incubated overnight at 4° C. After binding, the antibody solution is removed from the wells, which are then washed three times with 100 µl wash buffer (1×PBS/0.1% Tween-20). A total of 100 µl blocking buffer (1×PBS/0.1% Tween-20/0.1% BSA) is then added to each well and incubated for 2 hours at 22° C. Blocking buffer is then removed and the wells washed three times with wash buffer. Plasma or serum samples isolated from patients is then added to the wells in a volume of 100 µl in a dilution series, typically 1:1, 1:2, 1:5 and 1:10 dilutions, and is then incubated for 2 hours at 22° C. Plasma or serum samples are analyzed in duplicate.

Assays also include two standard curves. The first standard curve is prepared using dilutions of recombinant progastrin to a final amount of 1 ng, 0.5 ng, 0.25 ng, 0.1 ng, 0.05 ng, 0.01 ng, and 0 ng per well. The second standard curve, which serves as a negative control, is prepared from progastrin-negative human serum diluted in blocking buffer at the same dilutions as the test samples, i.e., 1:1, 1:2, 1:5 and 1:10. Alternatively, when plasma samples are being assayed, the second standard curve, which serves as a negative control, is prepared from progastrin-negative human plasma diluted in blocking buffer at the same dilutions as the test samples, i.e., 1:1, 1:2, 1:5 and 1:10.

After incubation with the plasma or serum samples is complete, the well contents are removed and the wells are washed three times with wash buffer, 100 µl/well, after which progastrin bound to the first antibody is detected using a second antibody specific for progastrin, as follows.

Biotin-coupled anti-progastrin monoclonal antibodies specific for the amino-terminal region of progastrin are diluted in blocking buffer to a concentration of 0.1 to 10 µl g/ml, depending on the antibody. A total of 100 µl of the antibody solution is then added to each well, and incubated for 1 hour at 22° C.

After secondary antibody binding is complete, the plates are washed three times with wash buffer, 100 µl/well, after which 100 µl of a solution of streptavidin-HRP (25 ng/ml in blocking buffer) is added to each well and incubated for 1 hour at 22° C. After incubation with the streptavidin-HRP solution is complete, the plates are washed three times with wash buffer, 100 µl/well. Thereafter, 100 µl of chemiluminescent substrate prepared using a Pierce SuperSignal ELISA Femto Maximum Sensitivity Chemiluminescent Substrate kit, is added per well, incubated for 5 min at room temperature in the dark, and then read on a luminometer.

Based on the luminometer readings, linear regression analysis is used to derive the equation of the lines corresponding to the standard curve data. Using this equation, the concentration of progastrin in the various patient samples is then calculated.

The median plasmatic concentration of progastrin is calculated in patients having prostate cancer and compared to the median plasmatic concentration of progastrin in plasma of control patients. These data demonstrate that patients with prostate cancer have elevated levels of progastrin in their plasma compared to healthy control individuals.

Example 3: Detection of Plasmatic Progastrin Concentration Using a Combination of Polyclonal Antibodies and Monoclonal Antibodies In the present example, plasma progastrin levels are quantified by ELISA through the use of antibody specific for human progastrin (hPG) pre-coated on a 96-well plate. Standards and samples are added to the wells, and any hPG present binds to the immobilized capture antibody. The wells are washed and an anti-hPG detection antibody horseradish peroxidase (HRP) conjugate is added, producing an antibody-antigen-antibody "sandwich." After a second wash, TMB substrate solution is added, which produces a blue color in direct proportion to the amount of hPG present in the initial sample. The Stop Solution changes color from blue to yellow, and the wells are read at 450 nm with a microplate reader.

Polyclonal antibodies are obtained by immunizing a rabbit with N-terminal progastrin (SEQ ID NO:2) or with C-terminal progastrin corresponding to amino acids 71 to 80 of hPG and having the sequence FGRRSAEDEN (SEQ ID NO:40), according to standard protocols.

Monoclonal antibodies are obtained by using hybridomas producing antibodies against N-terminal progastrin (SEQ ID NO:2) or against C-terminal progastrin corresponding to amino acids 71 to 80 of hPG and having the sequence FGRRSAEDEN (SEQ ID NO:40), according to standard protocols.

The binding characteristics of polyclonal and monoclonal antibodies against progastrin used in this assay are the following: absence of binding to G34-Gly, G34, G17-Gly, G17, binding to full length progastrin.

For the control test, ELISA in the presence of a known concentration of progastrin, progastrin dilution is prepared as follows: stock recombinant PG (Full length human progastrin produced in *E. coli* and affinity purified with Glutathione agarose/Tag removal (Tev)/IMAC Counter purification/dialysis, from Institut Pasteur, Paris, France) is prepared at a concentration of 0.45 mg/ml (45 microM), in triplicate. Ranges of progastrin concentrations are prepared as follows:

Solution A: Pre-dilution 1/10, 2 µl of stock+18 µl of the buffer

Solution B: Pre-dilution 1/100, 10 µl of A+90 µl of the buffer

Solution C: Pre-dilution 1/1000, 10 µl of B+90 µl of the buffer

Solution D: 500 pM, 5.55 µl of C+494.5 µl of the diluent
Solution E: 250 pM, 250 µl of D+250 µl of the diluent
Solution F: 100 pM, 200 µl of E+300 µl of the diluent
Solution G: 50 pM, 250 µl of F+250 µl of the diluent
Solution H: 25 pM, 200 µl of G+200 µl of the diluent
Solution I: 10 pM, 100 µl of H+150 µl of the diluent The range of recombinant PG is linear and can therefore be more or less extensive according to the antibody used.

Methods and Results

Progastrin levels are determined in plasma samples from subjects who were known to have developed prostate cancer later. Progastrin is captured with the C-terminus monoclonal antibody mAb 14 produced by hybridoma 2H9F4B7 described in WO 2011/083088 (Hybridoma 2H9F4B7 is deposited under the Budapest Treaty at the CNCM, Institut Pasteur, 25-28 rue du Docteur Roux, 75724 Paris CEDEX 15, France, on 27 Dec. 2016, under reference 1-5158.). Detection is performed with labelled polyclonal antibodies specific for the N-terminus.

The control is constituted by plasma samples from the general population.

The data demonstrate that patients with prostate cancer have detectable levels of progastrin in their plasma whereas healthy control individuals have none.

Example 4: Detection of Plasmatic Progastrin Concentration Using DECODE Lab Kit The test allows a measurement of hPG in plasma EDTA by ELISA.

The kit utilizes a capture antibody specific for hPG pre-coated on a 96-well plate. hPG present in standards and samples added to the wells was bound by the immobilized capture antibody. The wells were washed and an anti-hPG detection antibody horseradish peroxidase (HRP) conjugate was added, resulting in an antibody-antigen-antibody complex. After a second wash, a 3,3',5,5'-Tetramethylbenzidine (TMB) substrate solution was added to the well, producing a blue color in direct proportion to the amount of hPG present in the initial sample. The color of the Stop Solution changed from blue to yellow, and the wells were read at 450 nm with a microplate reader.

Methods and Results 40 plasma samples from prostate cancer patients and 119 plasma samples from healthy donors were used to measure the concentration of progastrin using the ELISA Kit DECODE Lab (capture antibody: Mab14, detection antibody: anti-hPG polyclonal) following manufacturer's recommendation.

Briefly:
1. Prepare all reagents, controls, and samples as directed in the previous section except the 1× Conjugate.
2. Remove excess strip from the microtiter plate frame, return them to the plate packet and store at 2-8° C.
3. Samples and controls must be tested in duplicate. Prepare the pre-loading of controls and samples by adding 65 µl/replicate in wells of the 96-Well DeepWell Polypropylene Microplates.
4. Add 50 µl of Sample dilution buffer to all the wells that will be used from the 96 pre-coated well plate strips included in the kit.
5. Transfer 50 µl of the controls and samples with a multi-channel pipette (8 channels) from the pre-loading 96-Well DeepWell Polypropylene Microplates to the 96 pre-coated well plate strips included in the kit. An example of the controls layout is given below. The loading time should not exceed 10 minutes.

|   | 1 | 2 | 3 | 4 | 5 | 6 | 7 | 8 |
|---|---|---|---|---|---|---|---|---|
| A | NC | NC | | | | | | |
| B | PC1 | PC1 | | | | | | |
| C | PC2 | PC2 | | | | | | |
| D | | | | | | | | |
| E | | | | | | | | |
| F | | | | | | | | |
| G | | | | | | | | |
| H | | | | | | | | |

6. Cover the plate with plastic paraffin and incubate for 3 h±5 min at 37° C. (±2° C.).
7. Prepare the 1× Conjugate as described in section 10.2
8. At the end of the incubation step, discard all the liquid from the wells by inverting the plate. Proceed to a thorough washing step by adding 300 µl per well of 1× Wash solution. Discard the 1× wash solution by inverting the plate and thoroughly pat dry the microtiter plate frame upside down on absorbent paper. Repeat the washing step 6 times. At the end of the washing steps, ensure the complete removal of the liquid from the wells: all liquid has been successfully removed when no sign of liquid remains on the paper towel. The wash procedure is critical. Insufficient washing may result in poor precision and falsely elevated absorbance readings.
9. Add 100 µl of the 1× Conjugate to each well.
10. Cover the plate with plastic paraffin and incubate 30 min±3 min at 21° C. (±5° C.).
11. At the end of the incubation step, discard all the liquid from the wells by inverting the plate. Proceed to a thorough washing step by adding 300 µl per well of 1× Wash solution. Discard the 1× wash solution by inverting the plate and thoroughly pat dry the microtiter plate frame upside down on absorbent paper. Repeat the washing step 6 times. At the end of the washing steps, ensure the complete removal of the liquid from the wells: all liquid has been successfully removed when no sign of liquid remains on the paper towel. The wash procedure is critical. Insufficient washing will result in poor precision and falsely elevated absorbance readings.
12. Add 100 µl of the Substrate solution to each well. Upon the addition of the Substrate solution, the content of the Positive Control 1 and Positive Control 2 wells should become blue.
13. Incubate for 15 min±2 min at 21° C. (±5° C.) in the dark.
14. Without removing the content, of the wells, add 100 µl of the Stop solution to each well in order to stop the reaction. Upon the addition of the Stop solution, the content of the Positive Control 1 and Positive Control 2 wells should become yellow.
15. Read and record the O.D. at 450 nm.

As shown in FIG. 1, the median plasmatic concentration of progastrin measured in control patients (n=119) was 0 pM, whereas a significant plasmatic concentration of progastrin was detected in patients having prostate cancer (n=40). Thus, patients with prostate cancer have higher levels of progastrin in their plasma than healthy control individuals.

The invention claimed is:

1. A method for the in vitro diagnosis of prostate cancer in a subject, said method comprising:
   a) obtaining a biological sample from said subject, wherein said biological sample is selected from the group consisting of blood, serum, and plasma;
   b) detecting whether progastrin is present in said biological sample by contacting said biological sample with a first progastrin-binding antibody, which binds to the C-terminal part of progastrin, defined by SEQ ID NO:3, wherein said first progastrin-binding antibody is a monoclonal antibody produced by the hybridoma deposited at the CNCM, Institut Pasteur, 25-28 rue du Docteur Roux, 75724 Paris CEDEX 15, France, on 27 Dec. 2016, under reference 1-5158 and a second progastrin-binding antibody, or an antigen-binding fragment thereof, which binds to the N-terminal part of progastrin, defined by SEQ ID NO:2, wherein said second progastrin-binding antibody is:
   a monoclonal antibody selected in the group consisting of:
   a monoclonal antibody comprising a heavy chain comprising CDR-H1, CDR-H2, and CDR-H3 of SEQ ID NO:4, SEQ ID NO:5, and SEQ ID NO:6, respectively, and a light chain comprising CDR-L1, CDR-L2, and CDR-L3 of SEQ ID NO:7, SEQ ID NO:8, and SEQ ID NO:9, respectively,
   a monoclonal antibody comprising a heavy chain comprising CDR-H1, CDR-H2, and CDR-H3 of SEQ ID NO:10, SEQ ID NO:11, and SEQ ID NO:12, respectively, and a light chain comprising CDR-L1, CDR-L2, and CDR-L3 of SEQ ID NO: 13, SEQ ID NO:14, and SEQ ID NO:15, respectively, a monoclonal antibody comprising a heavy chain comprising CDR-H1, CDR-H2, and CDR-H3 of SEQ ID NO:16, SEQ ID NO:17, and SEQ ID NO:18, respectively, and a light chain comprising CDR-L1, CDR-L2, and CDR-L3 of SEQ ID NO: 19, SEQ ID NO:20, and SEQ ID NO:21, respectively, and a monoclonal antibody comprising a heavy chain comprising CDR-H1, CDR-H2, and CDR-H3 of SEQ ID NO:22, SEQ ID NO:23, and SEQ ID NO:24, respectively, and a light chain comprising CDR-L1, CDR-L2, and CDR-L3 of SEQ ID NO:25, SEQ ID NO:26, and SEQ ID NO:27, respectively, or a polyclonal antibody binding an epitope within the N-terminus of progastrin;

and detecting the binding between progastrin and said first progastrin-binding antibody and said second progastrin-binding antibody;

c) detecting whether a prostate cancer biomarker is present in said biological sample; and d) diagnosing said subject with prostate cancer when the presence of progastrin and said prostate cancer biomarker is detected.

2. A method for the in vitro diagnosis of prostate cancer in a subject, said method comprising:
a) obtaining a biological sample from a subject, wherein said biological sample is selected from the group consisting of blood, serum, and plasma;
b) determining a concentration of progastrin in said biological sample by contacting said biological sample with
a first progastrin-binding antibody, which binds to the C-terminal part of progastrin, defined by SEQ ID NO:3, wherein said first progastrin-binding antibody is a monoclonal antibody produced by the hybridoma deposited at the CNCM, Institut Pasteur, 25-28 rue du Docteur Roux, 75724 Paris CEDEX 15, France, on 27 Dec. 2016, under reference 1-5158 and
a second progastrin-binding antibody, or an antigen-binding fragment thereof, which binds to the N-terminal part of progastrin, defined by SEQ ID NO:2, wherein said second progastrin-binding antibody is:
a monoclonal antibody selected in the group consisting of:
a monoclonal antibody comprising a heavy chain comprising CDR-H1, CDR-H2, and CDR-H3 of SEQ ID NO:4, SEQ ID NO:5, and SEQ ID NO:6, respectively, and a light chain comprising CDR-L1, CDR-L2, and CDR-L3 of SEQ ID NO:7, SEQ ID NO:8, and SEQ ID NO:9, respectively,
a monoclonal antibody comprising a heavy chain comprising CDR-H1, CDR-H2, and CDR-H3 of SEQ ID NO:10, SEQ ID NO:11, and SEQ ID NO:12, respectively, and a light chain comprising CDR-L1, CDR-L2, and CDR-L3 of SEQ ID NO:13, SEQ ID NO:14, and SEQ ID NO:15, respectively,
a monoclonal antibody comprising a heavy chain comprising CDR-H1, CDR-H2, and CDR-H3 of SEQ ID NO:16, SEQ ID NO:17, and SEQ ID NO:18, respectively, and a light chain comprising CDR-L1, CDR-L2, and CDR-L3 of SEQ ID NO:19, SEQ ID NO:20, and SEQ ID NO:21, respectively, and
a monoclonal antibody comprising a heavy chain comprising CDR-H1, CDR-H2, and CDR-H3 of SEQ ID NO:22, SEQ ID NO:23, and SEQ ID NO:24, respectively, and a light chain comprising CDR-L1, CDR-L2, and CDR-L3 of SEQ ID NO:25, SEQ ID NO:26, and SEQ ID NO:27, respectively, or a polyclonal antibody binding an epitope within the N-terminus of progastrin;

and detecting binding between progastrin and said first progastrin-binding antibody and said second progastrin-binding antibody;

c) detecting whether a prostate cancer biomarker is present in said biological sample; and d) diagnosing the subject with prostate cancer when the concentration of progastrin is at least 10 pM in said biological sample and the presence of said prostate cancer biomarker is detected.

3. A method for the in vitro diagnosis of prostate cancer in a subject, said method comprising:
a) obtaining a biological sample from a subject, wherein said biological sample is selected from the group consisting of blood, serum, and plasma;
b) determining a concentration of progastrin in said biological sample by contacting said biological sample with
a first progastrin-binding antibody, which binds to the C-terminal part of progastrin, defined by SEQ ID NO:3, wherein said first progastrin-binding antibody is a monoclonal antibody produced by the hybridoma deposited at the CNCM, Institut Pasteur, 25-28 rue du Docteur Roux, 75724 Paris CEDEX 15, France, on 27 Dec. 2016, under reference 1-5158 and
a second progastrin-binding antibody, or an antigen-binding fragment thereof, which binds to the N-terminal part of progastrin, defined by SEQ ID NO:2, wherein said second progastrin-binding antibody is:
a monoclonal antibody selected in the group consisting of:
a monoclonal antibody comprising a heavy chain comprising CDR-H1, CDR-H2, and CDR-H3 of SEQ ID NO:4, SEQ ID NO:5, and SEQ ID NO:6, respectively, and a light chain comprising CDR-L1, CDR-L2, and CDR-L3 of SEQ ID NO:7, SEQ ID NO:8, and SEQ ID NO:9, respectively,
a monoclonal antibody comprising a heavy chain comprising CDR-H1, CDR-H2, and CDR-H3 of SEQ ID NO:10, SEQ ID NO:11, and SEQ ID NO:12, respectively, and a light chain comprising CDR-L1, CDR-L2, and CDR-L3 of SEQ ID NO:13, SEQ ID NO:14, and SEQ ID NO:15, respectively,
a monoclonal antibody comprising a heavy chain comprising CDR-H1, CDR-H2, and CDR-H3 of SEQ ID NO:16, SEQ ID NO:17, and SEQ ID NO:18, respectively, and a light chain comprising CDR-L1, CDR-L2, and CDR-L3 of SEQ ID NO:19, SEQ ID NO:20, and SEQ ID NO:21, respectively, and
a monoclonal antibody comprising a heavy chain comprising CDR-H1, CDR-H2, and CDR-H3 of SEQ ID NO:22, SEQ ID NO:23, and SEQ ID NO:24, respectively, and a light chain comprising CDR-L1, CDR-L2, and CDR-L3 of SEQ ID NO:25, SEQ ID NO:26, and SEQ ID NO:27, respectively, or a polyclonal antibody binding an epitope within the N-terminus of progastrin;

and detecting the binding between progastrin and said first progastrin-binding antibody and said second progastrin-binding antibody;

c) determining a reference concentration of progastrin in a reference sample;

d) comparing the concentration of progastrin in said biological sample with said reference concentration of progastrin;
e) detecting whether a prostate cancer biomarker is present in the biological sample; and
f) diagnosing the subject with prostate cancer when the concentration of progastrin is higher in said biological sample compared to said reference concentration and the presence of said prostate cancer biomarker is detected.

4. The method of claim 1, wherein said biological sample is plasma.

5. The method of claim 1, wherein said prostate cancer biomarker is selected from the group consisting of PSA, kallikreins, PCa antigen 3, TMPRSS2-ERG, SchLAP1, ERG, SPDEF, HOXC6, and DLX1.

6. The method of claim 2, wherein said prostate cancer biomarker is selected from the group consisting of PSA, kallikreins, PCa antigen 3, TMPRSS2-ERG, SchLAP1, ERG, SPDEF, HOXC6, and DLX1.

7. The method of claim 2, wherein said biological sample is plasma.

8. The method of claim 3, wherein said prostate cancer biomarker is selected from the group consisting of PSA, kallikreins, PCa antigen 3, TMPRSS2-ERG, SchLAP1, ERG, SPDEF, HOXC6, and DLX1.

9. The method of claim 3, wherein said biological sample is plasma.

10. The method of claim 1, wherein said second progastrin-binding antibody is a monoclonal antibody comprising a heavy chain comprising the following three CDRs, CDR-H1, CDR-H2, and CDR-H3 of amino acid sequences SEQ ID NO:16, SEQ ID NO:17, and SEQ ID NO:18, respectively, and a light chain comprising the following three CDRs, CDR-L1, CDR-L2, and CDR-L3 of amino acid sequences SEQ ID NO:19, SEQ ID NO:20, and SEQ ID NO:21, respectively.

11. The method of claim 1, wherein the first progastrin-binding antibody is bound to an insoluble or partly soluble carrier and the second progastrin-binding antibody, or the antigen-binding fragment thereof is labelled with a detectable moiety.

12. The method of claim 2, wherein said second progastrin-binding antibody is a monoclonal antibody comprising a heavy chain comprising the following three CDRs, CDR-H1, CDR-H2, and CDR-H3 of amino acid sequences SEQ ID NO:16, SEQ ID NO:17, and SEQ ID NO:18, respectively, and a light chain comprising the following three CDRs, CDR-L1, CDR-L2, and CDR-L3 of amino acid sequences SEQ ID NO:19, SEQ ID NO:20, and SEQ ID NO:21, respectively.

13. The method of claim 2, wherein the first progastrin-binding antibody is bound to an insoluble or partly soluble carrier and the second progastrin-binding antibody, or the antigen-binding fragment thereof is labelled with a detectable moiety.

14. The method of claim 3, wherein said second progastrin-binding antibody is a monoclonal antibody comprising a heavy chain comprising the following three CDRs, CDR-H1, CDR-H2, and CDR-H3 of amino acid sequences SEQ ID NO:16, SEQ ID NO:17, and SEQ ID NO:18, respectively, and a light chain comprising the following three CDRs, CDR-L1, CDR-L2, and CDR-L3 of amino acid sequences SEQ ID NO:19, SEQ ID NO:20, and SEQ ID NO:21, respectively.

15. The method of claim 3, wherein the first progastrin-binding antibody is bound to an insoluble or partly soluble carrier and the second progastrin-binding antibody, or the antigen-binding fragment thereof is labelled with a detectable moiety.

* * * * *

SEQUENCE LISTING

<160> NUMBER OF SEQ ID NOS: 78

<210> SEQ ID NO 1
<211> LENGTH: 80
<212> TYPE: PRT
<213> ORGANISM: Homo sapiens

<400> SEQUENCE: 1

Ser Trp Lys Pro Arg Ser Gln Gln Pro Asp Ala Pro Leu Gly Thr Gly
1               5                   10                  15

Ala Asn Arg Asp Leu Glu Leu Pro Trp Leu Glu Gln Gln Gly Pro Ala
            20                  25                  30

Ser His His Arg Arg Gln Leu Gly Pro Gln Gly Pro Pro His Leu Val
        35                  40                  45

Ala Asp Pro Ser Lys Lys Gln Gly Pro Trp Leu Glu Glu Glu Glu Glu
    50                  55                  60

Ala Tyr Gly Trp Met Asp Phe Gly Arg Arg Ser Ala Glu Asp Glu Asn
65                  70                  75                  80

<210> SEQ ID NO 2
<211> LENGTH: 14
<212> TYPE: PRT
<213> ORGANISM: Artificial
<220> FEATURE:
<223> OTHER INFORMATION: Amino acids 1-14 N-terminal extremity of human
      progastrin

<400> SEQUENCE: 2

Ser Trp Lys Pro Arg Ser Gln Gln Pro Asp Ala Pro Leu Gly
1               5                   10

<210> SEQ ID NO 3
<211> LENGTH: 26
<212> TYPE: PRT
<213> ORGANISM: Artificial
<220> FEATURE:
<223> OTHER INFORMATION: Amino acids 55-80 C-terminal extremity of human
      progastrin

<400> SEQUENCE: 3

Gln Gly Pro Trp Leu Glu Glu Glu Glu Glu Ala Tyr Gly Trp Met Asp
1               5                   10                  15

Phe Gly Arg Arg Ser Ala Glu Asp Glu Asn
            20                  25

<210> SEQ ID NO 4
<211> LENGTH: 8
<212> TYPE: PRT
<213> ORGANISM: Artificial
<220> FEATURE:
<223> OTHER INFORMATION: synthetic peptide

<400> SEQUENCE: 4

Gly Tyr Ile Phe Thr Ser Tyr Trp
1               5

<210> SEQ ID NO 5
<211> LENGTH: 8
<212> TYPE: PRT
<213> ORGANISM: Artificial
<220> FEATURE:
<223> OTHER INFORMATION: synthetic peptide

```
<400> SEQUENCE: 5

Phe Tyr Pro Gly Asn Ser Asp Ser
1               5

<210> SEQ ID NO 6
<211> LENGTH: 8
<212> TYPE: PRT
<213> ORGANISM: Artificial
<220> FEATURE:
<223> OTHER INFORMATION: synthetic peptide

<400> SEQUENCE: 6

Thr Arg Arg Asp Ser Pro Gln Tyr
1               5

<210> SEQ ID NO 7
<211> LENGTH: 11
<212> TYPE: PRT
<213> ORGANISM: Artificial
<220> FEATURE:
<223> OTHER INFORMATION: synthetic peptide

<400> SEQUENCE: 7

Gln Ser Ile Val His Ser Asn Gly Asn Thr Tyr
1               5                   10

<210> SEQ ID NO 8
<211> LENGTH: 3
<212> TYPE: PRT
<213> ORGANISM: Artificial
<220> FEATURE:
<223> OTHER INFORMATION: synthetic peptide

<400> SEQUENCE: 8

Lys Val Ser
1

<210> SEQ ID NO 9
<211> LENGTH: 9
<212> TYPE: PRT
<213> ORGANISM: Artificial
<220> FEATURE:
<223> OTHER INFORMATION: synthetic peptide

<400> SEQUENCE: 9

Phe Gln Gly Ser His Val Pro Phe Thr
1               5

<210> SEQ ID NO 10
<211> LENGTH: 7
<212> TYPE: PRT
<213> ORGANISM: Artificial
<220> FEATURE:
<223> OTHER INFORMATION: synthetic peptide

<400> SEQUENCE: 10

Gly Tyr Thr Phe Ser Ser Trp
1               5

<210> SEQ ID NO 11
<211> LENGTH: 8
<212> TYPE: PRT
<213> ORGANISM: Artificial
<220> FEATURE:
<223> OTHER INFORMATION: synthetic peptide
```

```
<400> SEQUENCE: 11

Phe Leu Pro Gly Ser Gly Ser Thr
1               5

<210> SEQ ID NO 12
<211> LENGTH: 11
<212> TYPE: PRT
<213> ORGANISM: Artificial
<220> FEATURE:
<223> OTHER INFORMATION: synthetic peptide

<400> SEQUENCE: 12

Ala Thr Asp Gly Asn Tyr Asp Trp Phe Ala Tyr
1               5                   10

<210> SEQ ID NO 13
<211> LENGTH: 11
<212> TYPE: PRT
<213> ORGANISM: Artificial
<220> FEATURE:
<223> OTHER INFORMATION: synthetic peptide

<400> SEQUENCE: 13

Gln Ser Leu Val His Ser Ser Gly Val Thr Tyr
1               5                   10

<210> SEQ ID NO 14
<211> LENGTH: 3
<212> TYPE: PRT
<213> ORGANISM: Artificial
<220> FEATURE:
<223> OTHER INFORMATION: synthetic peptide

<400> SEQUENCE: 14

Lys Val Ser
1

<210> SEQ ID NO 15
<211> LENGTH: 9
<212> TYPE: PRT
<213> ORGANISM: Artificial
<220> FEATURE:
<223> OTHER INFORMATION: synthetic peptide

<400> SEQUENCE: 15

Ser Gln Ser Thr His Val Pro Pro Thr
1               5

<210> SEQ ID NO 16
<211> LENGTH: 8
<212> TYPE: PRT
<213> ORGANISM: Artificial
<220> FEATURE:
<223> OTHER INFORMATION: synthetic peptide

<400> SEQUENCE: 16

Gly Tyr Thr Phe Thr Ser Tyr Tyr
1               5

<210> SEQ ID NO 17
<211> LENGTH: 8
<212> TYPE: PRT
<213> ORGANISM: Artificial
<220> FEATURE:
<223> OTHER INFORMATION: synthetic peptide
```

```
<400> SEQUENCE: 17

Ile Asn Pro Ser Asn Gly Gly Thr
1               5

<210> SEQ ID NO 18
<211> LENGTH: 10
<212> TYPE: PRT
<213> ORGANISM: Artificial
<220> FEATURE:
<223> OTHER INFORMATION: synthetic peptide

<400> SEQUENCE: 18

Thr Arg Gly Gly Tyr Tyr Pro Phe Asp Tyr
1               5                   10

<210> SEQ ID NO 19
<211> LENGTH: 11
<212> TYPE: PRT
<213> ORGANISM: Artificial
<220> FEATURE:
<223> OTHER INFORMATION: synthetic peptide

<400> SEQUENCE: 19

Gln Ser Leu Leu Asp Ser Asp Gly Lys Thr Tyr
1               5                   10

<210> SEQ ID NO 20
<211> LENGTH: 3
<212> TYPE: PRT
<213> ORGANISM: Artificial
<220> FEATURE:
<223> OTHER INFORMATION: synthetic peptide

<400> SEQUENCE: 20

Leu Val Ser
1

<210> SEQ ID NO 21
<211> LENGTH: 9
<212> TYPE: PRT
<213> ORGANISM: Artificial
<220> FEATURE:
<223> OTHER INFORMATION: synthetic peptide

<400> SEQUENCE: 21

Trp Gln Gly Thr His Ser Pro Tyr Thr
1               5

<210> SEQ ID NO 22
<211> LENGTH: 9
<212> TYPE: PRT
<213> ORGANISM: Artificial
<220> FEATURE:
<223> OTHER INFORMATION: synthetic peptide

<400> SEQUENCE: 22

Gly Tyr Ser Ile Thr Ser Asp Tyr Ala
1               5

<210> SEQ ID NO 23
<211> LENGTH: 7
<212> TYPE: PRT
<213> ORGANISM: Artificial
<220> FEATURE:
<223> OTHER INFORMATION: synthetic peptide
```

```
<400> SEQUENCE: 23

Ile Ser Phe Ser Gly Tyr Thr
1               5

<210> SEQ ID NO 24
<211> LENGTH: 14
<212> TYPE: PRT
<213> ORGANISM: Artificial
<220> FEATURE:
<223> OTHER INFORMATION: synthetic peptide

<400> SEQUENCE: 24

Ala Arg Glu Val Asn Tyr Gly Asp Ser Tyr His Phe Asp Tyr
1               5                   10

<210> SEQ ID NO 25
<211> LENGTH: 7
<212> TYPE: PRT
<213> ORGANISM: Artificial
<220> FEATURE:
<223> OTHER INFORMATION: synthetic peptide

<400> SEQUENCE: 25

Ser Gln His Arg Thr Tyr Thr
1               5

<210> SEQ ID NO 26
<211> LENGTH: 7
<212> TYPE: PRT
<213> ORGANISM: Artificial
<220> FEATURE:
<223> OTHER INFORMATION: synthetic peptide

<400> SEQUENCE: 26

Val Lys Lys Asp Gly Ser His
1               5

<210> SEQ ID NO 27
<211> LENGTH: 13
<212> TYPE: PRT
<213> ORGANISM: Artificial
<220> FEATURE:
<223> OTHER INFORMATION: synthetic peptide

<400> SEQUENCE: 27

Gly Val Gly Asp Ala Ile Lys Gly Gln Ser Val Phe Val
1               5                   10

<210> SEQ ID NO 28
<211> LENGTH: 8
<212> TYPE: PRT
<213> ORGANISM: Artificial
<220> FEATURE:
<223> OTHER INFORMATION: synthetic peptide

<400> SEQUENCE: 28

Gly Phe Thr Phe Thr Thr Tyr Ala
1               5

<210> SEQ ID NO 29
<211> LENGTH: 8
<212> TYPE: PRT
<213> ORGANISM: Artificial
<220> FEATURE:
<223> OTHER INFORMATION: synthetic peptide
```

```
<400> SEQUENCE: 29

Ile Ser Ser Gly Gly Thr Tyr Thr
1               5

<210> SEQ ID NO 30
<211> LENGTH: 10
<212> TYPE: PRT
<213> ORGANISM: Artificial
<220> FEATURE:
<223> OTHER INFORMATION: synthetic peptide

<400> SEQUENCE: 30

Ala Thr Gln Gly Asn Tyr Ser Leu Asp Phe
1               5                   10

<210> SEQ ID NO 31
<211> LENGTH: 11
<212> TYPE: PRT
<213> ORGANISM: Artificial
<220> FEATURE:
<223> OTHER INFORMATION: synthetic peptide

<400> SEQUENCE: 31

Lys Ser Leu Arg His Thr Lys Gly Ile Thr Phe
1               5                   10

<210> SEQ ID NO 32
<211> LENGTH: 3
<212> TYPE: PRT
<213> ORGANISM: Artificial
<220> FEATURE:
<223> OTHER INFORMATION: synthetic peptide

<400> SEQUENCE: 32

Gln Met Ser
1

<210> SEQ ID NO 33
<211> LENGTH: 9
<212> TYPE: PRT
<213> ORGANISM: Artificial
<220> FEATURE:
<223> OTHER INFORMATION: synthetic peptide

<400> SEQUENCE: 33

Ala Gln Asn Leu Glu Leu Pro Leu Thr
1               5

<210> SEQ ID NO 34
<211> LENGTH: 8
<212> TYPE: PRT
<213> ORGANISM: Artificial
<220> FEATURE:
<223> OTHER INFORMATION: synthetic peptide

<400> SEQUENCE: 34

Gly Phe Ile Phe Ser Ser Tyr Gly
1               5

<210> SEQ ID NO 35
<211> LENGTH: 8
<212> TYPE: PRT
<213> ORGANISM: Artificial
<220> FEATURE:
<223> OTHER INFORMATION: synthetic peptide
```

```
<400> SEQUENCE: 35

Ile Asn Thr Phe Gly Asp Arg Thr
1               5

<210> SEQ ID NO 36
<211> LENGTH: 7
<212> TYPE: PRT
<213> ORGANISM: Artificial
<220> FEATURE:
<223> OTHER INFORMATION: synthetic peptide

<400> SEQUENCE: 36

Ala Arg Gly Thr Gly Thr Tyr
1               5

<210> SEQ ID NO 37
<211> LENGTH: 11
<212> TYPE: PRT
<213> ORGANISM: Artificial
<220> FEATURE:
<223> OTHER INFORMATION: synthetic peptide

<400> SEQUENCE: 37

Gln Ser Leu Leu Asp Ser Asp Gly Lys Thr Tyr
1               5                   10

<210> SEQ ID NO 38
<211> LENGTH: 3
<212> TYPE: PRT
<213> ORGANISM: Artificial
<220> FEATURE:
<223> OTHER INFORMATION: synthetic peptide

<400> SEQUENCE: 38

Leu Val Ser
1

<210> SEQ ID NO 39
<211> LENGTH: 9
<212> TYPE: PRT
<213> ORGANISM: Artificial
<220> FEATURE:
<223> OTHER INFORMATION: synthetic peptide

<400> SEQUENCE: 39

Trp Gln Gly Thr His Phe Pro Gln Thr
1               5

<210> SEQ ID NO 40
<211> LENGTH: 10
<212> TYPE: PRT
<213> ORGANISM: Artificial
<220> FEATURE:
<223> OTHER INFORMATION: Amino acids 71-80 C-terminal extremity of human
      progastrin

<400> SEQUENCE: 40

Phe Gly Arg Arg Ser Ala Glu Asp Glu Asn
1               5                   10

<210> SEQ ID NO 41
<211> LENGTH: 115
<212> TYPE: PRT
<213> ORGANISM: Artificial
<220> FEATURE:
<223> OTHER INFORMATION: synthetic peptide
```

```
<400> SEQUENCE: 41

Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Ile Phe Thr Ser Tyr
            20                  25                  30

Trp Val His Trp Val Lys Gln Arg Pro Gly Gln Gly Leu Glu Trp Ile
        35                  40                  45

Gly Gly Phe Tyr Pro Gly Asn Ser Asp Ser Arg Tyr Asn Gln Lys Phe
    50                  55                  60

Lys Gly Lys Ala Thr Leu Thr Ala Val Thr Ser Ala Ser Thr Ala Tyr
65                  70                  75                  80

Met Asp Leu Ser Ser Leu Thr Asn Glu Asp Ser Ala Val Tyr Phe Cys
                85                  90                  95

Thr Arg Arg Asp Ser Pro Gln Tyr Trp Gly Gln Gly Thr Thr Leu Thr
            100                 105                 110

Val Ser Ser
        115

<210> SEQ ID NO 42
<211> LENGTH: 112
<212> TYPE: PRT
<213> ORGANISM: Artificial
<220> FEATURE:
<223> OTHER INFORMATION: synthetic peptide

<400> SEQUENCE: 42

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Leu Glu Ala Glu Asp Leu Gly Val Tyr Tyr Cys Phe Gln Gly
                85                  90                  95

Ser His Val Pro Phe Thr Phe Gly Gly Gly Thr Lys Leu Glu Ile Lys
            100                 105                 110

<210> SEQ ID NO 43
<211> LENGTH: 118
<212> TYPE: PRT
<213> ORGANISM: Artificial
<220> FEATURE:
<223> OTHER INFORMATION: synthetic peptide

<400> SEQUENCE: 43

Gln Val Gln Leu Gln Gln Ser Gly Ala Glu Leu Met Lys Pro Gly Ala
1               5                   10                  15

Ser Val Lys Ile Ser Cys Lys Ala Thr Gly Tyr Thr Phe Ser Ser Ser
            20                  25                  30

Trp Ile Glu Trp Leu Lys Gln Arg Pro Gly His Gly Leu Glu Trp Ile
        35                  40                  45

Gly Glu Phe Leu Pro Gly Ser Gly Ser Thr Asp Tyr Asn Glu Lys Phe
    50                  55                  60
```

```
Lys Gly Lys Ala Thr Phe Thr Ala Asp Thr Ser Ser Asp Thr Ala Tyr
 65                  70                  75                  80

Met Leu Leu Ser Ser Leu Thr Ser Glu Asp Ser Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ala
        115

<210> SEQ ID NO 44
<211> LENGTH: 112
<212> TYPE: PRT
<213> ORGANISM: Artificial
<220> FEATURE:
<223> OTHER INFORMATION: synthetic peptide

<400> SEQUENCE: 44

Asp Leu Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
             20                  25                  30

Ser Gly Val Thr Tyr Leu His Trp Tyr Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Val Pro Pro Thr Phe Gly Ser Gly Thr Lys Leu Glu Ile Lys
            100                 105                 110

<210> SEQ ID NO 45
<211> LENGTH: 117
<212> TYPE: PRT
<213> ORGANISM: Artificial
<220> FEATURE:
<223> OTHER INFORMATION: synthetic peptide

<400> SEQUENCE: 45

Gln Val Gln Leu Gln Gln Ser Gly Ala Glu Leu Val Lys Pro Gly Ala
 1               5                  10                  15

Ser Val Lys Leu Ser Cys Lys Ala Ser Gly Tyr Thr Phe Thr Ser Tyr
             20                  25                  30

Tyr Met Tyr Trp Val Lys Gln Arg Pro Gly Gln Gly Leu Glu Trp Ile
         35                  40                  45

Gly Glu Ile Asn Pro Ser Asn Gly Gly Thr Asn Phe Asn Glu Lys Phe
 50                  55                  60

Lys Ser Lys Ala Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Thr Arg Gly Gly Tyr Tyr Pro Phe Asp Tyr Trp Gly Gln Gly Thr Thr
            100                 105                 110

Leu Thr Val Ser Ser
        115
```

```
<210> SEQ ID NO 46
<211> LENGTH: 112
<212> TYPE: PRT
<213> ORGANISM: Artificial
<220> FEATURE:
<223> OTHER INFORMATION: synthetic peptide

<400> SEQUENCE: 46

Asp Val Val Met Thr Gln Thr Pro Leu Thr Leu Ser Val Thr Ile Gly
1               5                   10                  15

Arg Pro Ala Ser Ile Ser Cys Lys Ser Gln Ser Leu Leu Asp Ser
            20                  25                  30

Asp Gly Lys Thr Tyr Leu Tyr Trp Leu Leu Gln Arg Pro Gly Gln Ser
        35                  40                  45

Pro Lys Arg Leu Ile Tyr Leu Val Ser Glu Leu Asp Ser Gly Val Pro
    50                  55                  60

Asp Arg Ile Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Ser Pro Tyr Thr Phe Gly Gly Gly Thr Lys Leu Glu Ile Lys
            100                 105                 110

<210> SEQ ID NO 47
<211> LENGTH: 121
<212> TYPE: PRT
<213> ORGANISM: Artificial
<220> FEATURE:
<223> OTHER INFORMATION: synthetic peptide

<400> SEQUENCE: 47

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Ser Phe Ser Gly Tyr Thr Ser Tyr Asn Pro Ser Leu
    50                  55                  60

Lys Ser Arg Ile Ser Val Thr Arg Asp Thr Ser Arg Asn Gln Phe Phe
65                  70                  75                  80

Leu Gln Leu Thr Ser Val Thr Thr Glu Asp Thr Ala Thr Tyr Tyr Cys
                85                  90                  95

Ala Arg Glu Val Asn Tyr Gly Asp Ser Tyr His Phe Asp Tyr Trp Gly
            100                 105                 110

Gln Gly Thr Ile Val Thr Val Ser Ser
        115                 120

<210> SEQ ID NO 48
<211> LENGTH: 115
<212> TYPE: PRT
<213> ORGANISM: Artificial
<220> FEATURE:
<223> OTHER INFORMATION: synthetic peptide

<400> SEQUENCE: 48

Gln Leu Ala Leu Thr Gln Ser Ser Ser Ala Ser Phe Ser Leu Gly Ala
1               5                   10                  15

Ser Ala Lys Leu Thr Cys Thr Leu Ser Ser Gln His Arg Thr Tyr Thr
            20                  25                  30
```

```
Ile Glu Trp Tyr Gln Gln Gln Ser Leu Lys Pro Pro Lys Tyr Val Met
        35                  40                  45

Glu Val Lys Lys Asp Gly Ser His Ser Thr Gly His Gly Ile Pro Asp
 50                  55                  60

Arg Phe Ser Gly Ser Ser Ser Gly Ala Asp Arg Tyr Leu Ser Ile Ser
 65                  70                  75                  80

Asn Ile Gln Pro Glu Asp Glu Ala Ile Tyr Ile Cys Gly Val Gly Asp
                 85                  90                  95

Ala Ile Lys Gly Gln Ser Val Phe Val Phe Gly Gly Thr Lys Val
            100                 105                 110

Thr Val Leu
        115

<210> SEQ ID NO 49
<211> LENGTH: 117
<212> TYPE: PRT
<213> ORGANISM: Artificial
<220> FEATURE:
<223> OTHER INFORMATION: synthetic peptide

<400> SEQUENCE: 49

Glu Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Thr Thr Tyr
             20                  25                  30

Ala Met Ser Trp Val Arg Gln Ala Pro Gly Lys Gly Leu Glu Trp Val
         35                  40                  45

Ala Thr Ile Ser Ser Gly Gly Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Thr Gln Gly Asn Tyr Ser Leu Asp Phe Trp Gly Gln Gly Thr Thr
            100                 105                 110

Val Thr Val Ser Ser
        115

<210> SEQ ID NO 50
<211> LENGTH: 112
<212> TYPE: PRT
<213> ORGANISM: Artificial
<220> FEATURE:
<223> OTHER INFORMATION: synthetic peptide

<400> SEQUENCE: 50

Asp Ile Val Met Thr Gln Ser Pro Leu Ser Leu Pro Val Thr Pro Gly
  1               5                  10                  15

Glu Pro Ala Ser Ile Ser Cys Arg Ser Ser Lys Ser Leu Arg His Thr
             20                  25                  30

Lys Gly Ile Thr Phe Leu Tyr Trp Tyr Leu Gln Lys Pro Gly Gln Ser
         35                  40                  45

Pro Gln Leu Leu Ile Tyr Gln Met Ser Asn Leu Ala Ser Gly Val Pro
 50                  55                  60

Asp Arg Phe Ser Ser Ser Gly Ser Gly Thr Asp Phe Thr Leu Lys Ile
 65                  70                  75                  80
```

-continued

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 51
<211> LENGTH: 114
<212> TYPE: PRT
<213> ORGANISM: Artificial
<220> FEATURE:
<223> OTHER INFORMATION: synthetic peptide

<400> SEQUENCE: 51

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Ile Phe Ser Ser Tyr
            20                  25                  30

Gly Met Ser Trp Val Arg Gln Ser Pro Asp Arg Arg Leu Glu Leu Val
        35                  40                  45

Ala Ser Ile Asn Thr Phe Gly Asp Arg Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Thr Ser Leu Lys Ser Glu Asp Thr Ala Ile Tyr Tyr Cys
                85                  90                  95

Ala Arg Gly Thr Gly Thr Tyr Trp Gly Gln Gly Thr Thr Leu Thr Val
            100                 105                 110

Ser Ser

<210> SEQ ID NO 52
<211> LENGTH: 112
<212> TYPE: PRT
<213> ORGANISM: Artificial
<220> FEATURE:
<223> OTHER INFORMATION: synthetic peptide

<400> SEQUENCE: 52

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Gln Thr Phe Gly Gly Gly Thr Lys Leu Glu Ile Lys
            100                 105                 110

<210> SEQ ID NO 53
<211> LENGTH: 115
<212> TYPE: PRT
<213> ORGANISM: Artificial
<220> FEATURE:
<223> OTHER INFORMATION: synthetic peptide

```
<400> SEQUENCE: 53

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Ser Tyr
                20                  25                  30

Trp Val His Trp Val Arg Gln Ala Pro Gly Gln Arg Leu Glu Trp Met
            35                  40                  45

Gly Gly Phe Tyr Pro Gly Asn Ser Asp Ser Arg Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Thr Arg Arg Asp Ser Pro Gln Tyr Trp Gly Gln Gly Thr Leu Val Thr
            100                 105                 110

Val Ser Ser
        115

<210> SEQ ID NO 54
<211> LENGTH: 112
<212> TYPE: PRT
<213> ORGANISM: Artificial
<220> FEATURE:
<223> OTHER INFORMATION: synthetic peptide

<400> SEQUENCE: 54

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asn Gly Asn Thr Tyr Leu Glu Trp Phe Gln Gln Arg Pro Gly Gln Ser
            35                  40                  45

Pro Arg Arg Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Phe Thr Phe Gly Gly Gly Thr Lys Val Glu Ile Lys
            100                 105                 110

<210> SEQ ID NO 55
<211> LENGTH: 118
<212> TYPE: PRT
<213> ORGANISM: Artificial
<220> FEATURE:
<223> OTHER INFORMATION: synthetic peptide

<400> SEQUENCE: 55

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Ser Ser
                20                  25                  30

Trp Met His Trp Val Arg Gln Ala Pro Gly Gln Gly Leu Glu Trp Met
            35                  40                  45

Gly Ile Phe Leu Pro Gly Ser Gly Ser Thr Asp Tyr Ala Gln Lys Phe
    50                  55                  60
```

```
Gln Gly Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Thr Asp Gly Asn Tyr Asp Trp Phe Ala Tyr Trp Gly Gln Gly Thr
            100                 105                 110

Leu Val Thr Val Ser Ser
        115

<210> SEQ ID NO 56
<211> LENGTH: 112
<212> TYPE: PRT
<213> ORGANISM: Artificial
<220> FEATURE:
<223> OTHER INFORMATION: synthetic peptide

<400> SEQUENCE: 56

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Val His Ser
            20                  25                  30

Ser Gly Val Thr Tyr Leu Tyr Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Pro Thr Phe Gly Gln Gly Thr Lys Leu Glu Ile Lys
            100                 105                 110

<210> SEQ ID NO 57
<211> LENGTH: 117
<212> TYPE: PRT
<213> ORGANISM: Artificial
<220> FEATURE:
<223> OTHER INFORMATION: synthetic peptide

<400> SEQUENCE: 57

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met Tyr Trp Val Arg Gln Ala Pro Gly Gln Gly Leu Glu Trp Met
        35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
            100                 105                 110

Val Thr Val Ser Ser
        115
```

<210> SEQ ID NO 58
<211> LENGTH: 117
<212> TYPE: PRT
<213> ORGANISM: Artificial
<220> FEATURE:
<223> OTHER INFORMATION: synthetic peptide

<400> SEQUENCE: 58

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Asn Gly Gly Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
            115

<210> SEQ ID NO 59
<211> LENGTH: 117
<212> TYPE: PRT
<213> ORGANISM: Artificial
<220> FEATURE:
<223> OTHER INFORMATION: synthetic peptide

<400> SEQUENCE: 59

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met Tyr Trp Val Arg Gln Ala Pro Gly Gln Gly Leu Glu Trp Met
            35                  40                  45

Gly Glu Ile Asn Pro Ser Asn Gly Gly Thr Asn Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Thr Arg Gly Gly Tyr Tyr Pro Phe Asp Tyr Trp Gly Gln Gly Thr Thr
                100                 105                 110

Val Thr Val Ser Ser
            115

<210> SEQ ID NO 60
<211> LENGTH: 112
<212> TYPE: PRT
<213> ORGANISM: Artificial
<220> FEATURE:
<223> OTHER INFORMATION: synthetic peptide

```
<400> SEQUENCE: 60

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 61
<211> LENGTH: 112
<212> TYPE: PRT
<213> ORGANISM: Artificial
<220> FEATURE:
<223> OTHER INFORMATION: synthetic peptide

<400> SEQUENCE: 61

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 62
<211> LENGTH: 112
<212> TYPE: PRT
<213> ORGANISM: Artificial
<220> FEATURE:
<223> OTHER INFORMATION: synthetic peptide

<400> SEQUENCE: 62

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Tyr Trp Phe Gln Gln Arg Pro Gly Gln Ser
        35                  40                  45

Pro Arg Arg Leu Ile Tyr Leu Val Ser Glu Arg Asp Ser Gly Val Pro
    50                  55                  60

Asp Arg Phe Ser Gly Ser Gly Ser Gly Thr Asp Phe Thr Leu Lys Ile
65                  70                  75                  80
```

Ser Arg Val Glu Ala Glu Asp Val Gly Val Tyr Tyr Cys Trp Gln Gly
                85                  90                  95

Thr His Ser Pro Tyr Thr Phe Gly Gln Gly Thr Lys Leu Glu Ile Lys
            100                 105                 110

<210> SEQ ID NO 63
<211> LENGTH: 121
<212> TYPE: PRT
<213> ORGANISM: Artificial
<220> FEATURE:
<223> OTHER INFORMATION: synthetic peptide

<400> SEQUENCE: 63

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 64
<211> LENGTH: 121
<212> TYPE: PRT
<213> ORGANISM: Artificial
<220> FEATURE:
<223> OTHER INFORMATION: synthetic peptide

<400> SEQUENCE: 64

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Ser Trp Ile Arg Gln His Pro Gly Lys Gly Leu Glu Trp
        35                  40                  45

Ile Gly Tyr Ile Ser Phe Ser Gly Tyr Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 65
<211> LENGTH: 121
<212> TYPE: PRT
<213> ORGANISM: Artificial

<220> FEATURE:
<223> OTHER INFORMATION: synthetic peptide

<400> SEQUENCE: 65

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Ser Asp
            20                  25                  30

Tyr Ala Trp Asn Trp Ile Arg Gln His Pro Gly Lys Gly Leu Glu Trp
        35                  40                  45

Ile Gly Tyr Ile Ser Phe Ser Gly Tyr Thr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Val Asn Tyr Gly Asp Ser Tyr His Phe Asp Tyr Trp Gly
            100                 105                 110

Gln Gly Thr Leu Val Thr Val Ser Ser
        115                 120

<210> SEQ ID NO 66
<211> LENGTH: 115
<212> TYPE: PRT
<213> ORGANISM: Artificial
<220> FEATURE:
<223> OTHER INFORMATION: synthetic peptide

<400> SEQUENCE: 66

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

Ile Glu Trp His Gln Gln Gln Pro Glu Lys Gly Pro Arg Tyr Leu Met
        35                  40                  45

Lys Val Lys Lys Asp Gly Ser His Ser Lys Gly Asp Gly Ile Pro Asp
    50                  55                  60

Arg Phe Ser Gly Ser Ser Ser Gly Ala Glu Arg Tyr Leu Thr Ile Ser
65                  70                  75                  80

Ser Leu Gln Ser Glu Asp Glu Ala Asp Tyr Tyr Cys Gly Val Gly Asp
                85                  90                  95

Ala Ile Lys Gly Gln Ser Val Phe Val Phe Gly Gly Gly Thr Lys Val
            100                 105                 110

Glu Ile Lys
        115

<210> SEQ ID NO 67
<211> LENGTH: 115
<212> TYPE: PRT
<213> ORGANISM: Artificial
<220> FEATURE:
<223> OTHER INFORMATION: synthetic peptide

<400> SEQUENCE: 67

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gln His Arg Thr Tyr Thr
            20                  25                  30

```
Ile Ala Trp His Gln Gln Pro Glu Lys Gly Pro Arg Tyr Leu Met
            35                  40                  45

Lys Val Lys Lys Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
                100                 105                 110

Glu Ile Lys
        115

<210> SEQ ID NO 68
<211> LENGTH: 115
<212> TYPE: PRT
<213> ORGANISM: Artificial
<220> FEATURE:
<223> OTHER INFORMATION: synthetic peptide

<400> SEQUENCE: 68

Gln Leu Val Leu Thr Gln Ser Pro Ser Ala Ser Ala Ser Leu Gly Ala
 1               5                  10                  15

Ser Val Lys Leu Thr Cys Thr Leu Ser Ser Gln His Arg Thr Tyr Thr
                20                  25                  30

Ile Glu Trp His Gln Gln Pro Glu Lys Gly Pro Arg Tyr Leu Met
            35                  40                  45

Glu Val Lys Lys Asp Gly Ser His Ser Lys Gly Asp Gly Ile Pro Asp
 50                  55                  60

Arg Phe Ser Gly Ser Ser Gly Ala Glu Arg Tyr Leu Thr Ile Ser
 65                  70                  75                  80

Ser Leu Gln Ser Glu Asp Glu Ala Asp Tyr Tyr Cys Gly Val Gly Asp
                 85                  90                  95

Ala Ile Lys Gly Gln Ser Val Phe Val Phe Gly Gly Gly Thr Lys Val
                100                 105                 110

Glu Ile Lys
        115

<210> SEQ ID NO 69
<211> LENGTH: 117
<212> TYPE: PRT
<213> ORGANISM: Artificial
<220> FEATURE:
<223> OTHER INFORMATION: synthetic peptide

<400> SEQUENCE: 69

Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Thr Thr Tyr
                20                  25                  30

Ala Met Ser Trp Val Arg Gln Ala Pro Gly Lys Gly Leu Glu Trp Val
            35                  40                  45

Ser Ser Ile Ser Ser Gly Gly Thr Tyr Thr Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ala Thr Gln Gly Asn Tyr Ser Leu Asp Phe Trp Gly Gln Gly Thr Thr
                100                 105                 110

Val Thr Val Ser Ser
        115

<210> SEQ ID NO 70
<211> LENGTH: 112
<212> TYPE: PRT
<213> ORGANISM: Artificial
<220> FEATURE:
<223> OTHER INFORMATION: synthetic peptide

<400> SEQUENCE: 70

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
                100                 105                 110

<210> SEQ ID NO 71
<211> LENGTH: 117
<212> TYPE: PRT
<213> ORGANISM: Artificial
<220> FEATURE:
<223> OTHER INFORMATION: synthetic peptide

<400> SEQUENCE: 71

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
                100                 105                 110

Val Thr Val Ser Ser
        115

<210> SEQ ID NO 72
<211> LENGTH: 112
<212> TYPE: PRT
<213> ORGANISM: Artificial
<220> FEATURE:
<223> OTHER INFORMATION: synthetic peptide
```

<400> SEQUENCE: 72

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

<210> SEQ ID NO 73
<211> LENGTH: 447
<212> TYPE: PRT
<213> ORGANISM: Artificial
<220> FEATURE:
<223> OTHER INFORMATION: synthetic peptide

<400> SEQUENCE: 73

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Thr Thr Tyr
            20                  25                  30

Ala Met Ser Trp Val Arg Gln Ala Pro Gly Lys Gly Leu Glu Trp Val
        35                  40                  45

Ala Thr Ile Ser Ser Gly Gly Thr Tyr Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Gln Gly Asn Tyr Ser Leu Asp Phe Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

```
Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 74
<211> LENGTH: 219
<212> TYPE: PRT
<213> ORGANISM: Artificial
<220> FEATURE:
<223> OTHER INFORMATION: synthetic peptide

<400> SEQUENCE: 74

Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Arg His Thr
            20                  25                  30

Lys Gly Ile Thr Phe Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
              165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 75
<211> LENGTH: 114
<212> TYPE: PRT
<213> ORGANISM: Artificial
<220> FEATURE:
<223> OTHER INFORMATION: synthetic peptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Asn Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

<210> SEQ ID NO 76
<211> LENGTH: 114
<212> TYPE: PRT
<213> ORGANISM: Artificial
<220> FEATURE:
<223> OTHER INFORMATION: synthetic peptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Phe Ser Ser Tyr
            20                  25                  30

Gly Met Ser Trp Val Arg Gln Ala Pro Gly Lys Gly Leu Glu Trp Val
        35                  40                  45

Ala Ser Ile Asn Thr Phe Gly Asp Arg Thr Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Thr Gly Thr Tyr Trp Gly Gln Gly Thr Leu Val Thr Val
            100                 105                 110

Ser Ser

```
<210> SEQ ID NO 77
<211> LENGTH: 112
<212> TYPE: PRT
<213> ORGANISM: Artificial
<220> FEATURE:
<223> OTHER INFORMATION: synthetic peptide

<400> SEQUENCE: 77

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110

<210> SEQ ID NO 78
<211> LENGTH: 112
<212> TYPE: PRT
<213> ORGANISM: Artificial
<220> FEATURE:
<223> OTHER INFORMATION: synthetic peptide

<400> SEQUENCE: 78

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Leu Asp Ser
            20                  25                  30

Asp Gly Lys Thr Tyr Leu Asn Trp Phe Gln Gln Arg Pro Gly Gln Ser
        35                  40                  45

Pro Arg Arg Leu Ile Tyr Leu Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Trp Gln Gly
                85                  90                  95

Thr His Phe Pro Gln Thr Phe Gly Gly Gly Thr Lys Val Glu Ile Lys
            100                 105                 110
```